(12) United States Patent
Ly et al.

(10) Patent No.: US 8,507,005 B2
(45) Date of Patent: Aug. 13, 2013

(54) PARTICULATES OF A CRTH2 ANTAGONIST

(75) Inventors: Tai Wei Ly, San Diego, CA (US); Hui-Yin Li, Hockessin, DE (US)

(73) Assignee: Actimis Pharmaceuticals, Inc., San Diego, CA (US)

( * ) Notice: Subject to any disclaimer, the term of this patent is extended or adjusted under 35 U.S.C. 154(b) by 423 days.

(21) Appl. No.: 12/665,706

(22) PCT Filed: Jun. 18, 2008

(86) PCT No.: PCT/US2008/007589
§ 371 (c)(1),
(2), (4) Date: Nov. 12, 2010

(87) PCT Pub. No.: WO2008/156780
PCT Pub. Date: Dec. 24, 2008

(65) Prior Publication Data
US 2011/0052701 A1 Mar. 3, 2011

Related U.S. Application Data

(60) Provisional application No. 60/936,972, filed on Jun. 21, 2007.

(51) Int. Cl.
*A61K 9/14* (2006.01)
*C07D 239/46* (2006.01)
*A61K 31/505* (2006.01)
*A61P 17/06* (2006.01)
*A61P 17/00* (2006.01)
*B32B 5/16* (2006.01)

(52) U.S. Cl.
USPC ............ 424/489; 544/322; 514/256; 428/402

(58) Field of Classification Search
None
See application file for complete search history.

(56) References Cited

FOREIGN PATENT DOCUMENTS

| ES | WO2004/096777 | * 11/2004 |
|---|---|---|
| WO | WO 2004/096777 | 11/2004 |

OTHER PUBLICATIONS

Ly and Bacon, "Small-molecule CRTH2 antagonists for the treatment of allergic inflammation: an overview," *Expert Opin. Investig. Drugs* 2005, 14, 769-773.
Nagata et al., "Selective expression of a novel surface molecule by human Th2 cells in vivo," *J. Immunol.* 162, 1278-1286 (1999).
Hirai et al., "Prostaglandin D2 selectively induces chemotaxis in T helper type 2 cells, eosinophils, and basophils via seven-transmembrane receptor CRTH2," *J. Exp. Med.* 193, 255-261 (2001).
Gervais et al., "Selective modulation of chemokinesis, degranulation, and apoptosis in eosinophils through the PGD2 receptors CRTH2 and DP," *J. Allergy Clin. Immunol.* 108, 982-988 (2001).
Cosmi et al., "CRTH2 is the most reliable marker for the detection of circulating human type 2 Th and type 2 T cytotoxic cells in health and disease," *Eur. J. Immunol.*, 30, 2972-2979 (2000).
Iwazaki et al., "Association of a new-type prostaglandin D2 receptor CRTH2 with circulating T helper 2 cells in patients with atopic dermatitis," *J. Investigative Dermatology* 119, 609-616 (2002).
Fujitani et al., "Pronounced eosinophilic lung inflammation and Th2 cytokine release in human lipocalin-type prostaglandin D synthase transgenic mice," *J. Immunol.*, 168, 443-449 (2002).
Sugimoto et al., "An orally bioavailable small molecule antagonist of CRTH2, ramatroban (BAY u3405), inhibits prostaglandin $D_2$-induced eosinophil migration in vitro," *J. Pharm. Exp. Therap.*, 305, 347-352 (2003).
Sugimoto et al., "CRTH2-Specific binding characteristics of [$^3$H]ramatroban and its effects on $PGD_2$-, 15-deoxy-$\Delta^{12, 14}$-$PGJ_2$- and indomethacin-induced agonist responses," *Eur. J. Pharmacol.*, 524, 30-37 (2005).
Narumiya et al., "Prostanoid receptors: structures, properties and functions," *Physiol. Revs.*, 79, 1193-1226 (1999).
Hamilos et al., "Eosinophil infiltration in nonallergic chronic hyperplastic sinusitis with nasal polyposis (CHS/NP) is associated with endothelial VCAM-1 upregulation and expression of TNF-α," *Am. J. Resp. Cell Mol. Biol.*, 15, 443-450 (1996).
Misumori, "Recent progress in work on PGD2 antagonists for drugs targeting allergic diseases," *Curr. Pharm. Design*, 10, 3533-3538 (2004).
Nagata et al., "CRTH2, An orphan receptor of T-helper-2 cells, is expressed on basophils and eosinophils and responds to mast-cell-derived factor(s),"*FEBS Lett.*, 459, 195-199 (1999).
Shichijo et al., "Chemoattractant receptor-homologous molecule expressed on Th2 cells activation in vivo increases blood leukocyte counts and its blockade abrogates 13,14-dihydro-15-keto prostaglandin D2-induced eosinophilia in rats,"*J. Pharm. Exp. Therap.*, 307, 518-525 (2003).
Cheng et al., "Relationship between the inhibition constant Ki and the concentration of inhibitor which causes 50% inhibition ($IC_{50}$) of an enzymatic reaction," *Biochem. Pharmacol.*, 22, 3099-3108 (1973).
Grynkiewicz et al., "A new generation of $Ca^{2+}$ indicators with greatly improved fluorescence properties," , *J. Biol. Chem.*, 260, 3440-3450 (1985).
Peterson et al., "Expanding the scope of crystal form evaluation in pharmaceutical science," J. Pharm. Pharmaceut. Sci., 2006, 9, 317-326.
Bernstein, "Crystal structure prediction and polymorphism," ACA Transactions, 2004, 39, 14-23.

\* cited by examiner

*Primary Examiner* — Mina Haghighatian
*Assistant Examiner* — Erin Hirt
(74) *Attorney, Agent, or Firm* — Jones Day

(57) ABSTRACT

Provided herein are particulates of {4,6-bis(dimethylamino)-2-(4-(4-(trifluoromethyl)benzamido)benzyl)pyrimidin-5-yl}acetic acid in amorphous or crystalline forms, processes for their preparation, pharmaceutical compositions comprising them, and methods of their use for treating, preventing, or ameliorating one or more symptoms of a CRTH2-mediated disorder or disease.

11 Claims, 11 Drawing Sheets

PARTICULATES OF A CRTH2 ANTAGONIST

CROSS REFERENCE TO RELATED APPLICATIONS

This application is a 371 of PCT/US2008/007589, filed Jun. 18, 2008, which claims priority to U.S. Provisional No. 60/936,972, filed Jun. 21, 2007, which is incorporated by reference in its entirety.

FIELD

Provided herein are particulates of {4,6-bis(dimethylamino)-2-(4-(4-(trifluoromethyl)benzamido)benzyl)pyrimidin-5-yl}acetic acid in amorphous and crystalline forms, processes of preparation, and pharmaceutical compositions thereof. Also provided are methods of their use for treating, preventing, or ameliorating one or more symptoms of a CRTH2-mediated disorder or disease.

BACKGROUND

CRTH2 is a G protein-coupled chemoattractant receptor expressed on Th2 cells, eosinophils, and basophils (Nagata et al., *J. Immunol.* 1999, 162, 1278-1286; Hirai et al., *J. Exp. Med.* 2001, 193, 255-261). Prostaglandin $D_2$ ($PGD_2$), the major inflammatory mediator produced from mast cells, is a natural ligand for CRTH2. Recently, it has been shown that the activation of CRTH2 by $PGD_2$ induces the migration and activation of Th2 cells and eosinophils, suggesting that CRTH2 may play a pro-inflammatory role in allergic diseases (Hirai et al., *J. Exp. Med.* 2001, 193, 255-261; Gervais et al., *J. Allergy Clin. Immunol.* 2001, 108, 982-988). It has also been shown that, in atopic dermatitis patients, there is an increase in circulating T cells expressing CRTH2, which correlates with the severity of the disease (Cosmi et al., *Eur. J. Immunol.* 2000, 30, 2972-2979; Iwazaki et al., *J. Investigative Dermatology* 2002, 119, 609-616). The role of $PGD_2$ in the initiation and maintenance of allergic inflammation has further been demonstrated in mouse models of asthma by showing that overproduction of $PGD_2$ in vivo by $PGD_2$ synthase exacerbates airway inflammation (Fujitani et al., *J. Immunol.* 2002, 168, 443-449). Therefore, CRTH2 antagonists are potentially useful for the treatment of CRTH2-mediated disorders or diseases, such as allergic rhinitis, allergic asthma, bronchoconstriction, atopic dermatitis, or systemic inflammatory disorders.

SUMMARY OF THE DISCLOSURE

Provided are particulates of {4,6-bis(dimethylamino)-2-(4-(4-(trifluoro-methyl)benzamido)benzyl)pyrimidin-5-yl}acetic acid, which has Formula I:

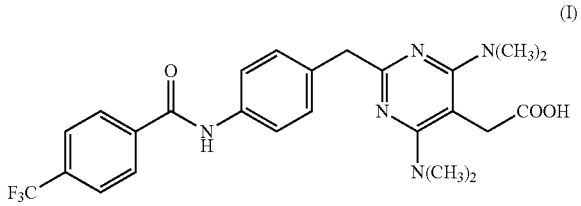

(I)

in an amorphous form, or crystalline Form I or II. The compound of Formula I has been identified as a CRTH2 antagonist (WO 2004/0022218).

In one embodiment, the particulates of {4,6-bis(dimethylamino)-2-(4-(4-(trifluoromethyl)benzamido)benzyl)pyrimidin-5-yl}acetic acid have Form I, which has an X-ray powder diffraction pattern substantially as shown in FIG. 1, or a differential scanning calorimetric thermogram substantially as shown in FIG. 2.

In another embodiment, the particulates of {4,6-bis(dimethylamino)-2-(4-(4-(trifluoromethyl)benzamido)benzyl)pyrimidin-5-yl}acetic acid have Form II, which has an X-ray powder diffraction pattern substantially as shown in FIG. 6.

In yet another embodiment, the particulates of {4,6-bis(dimethylamino)-2-(4-(4-(trifluoromethyl)benzamido)benzyl)pyrimidin-5-yl}acetic acid are amorphous.

Also provided is a pharmaceutical composition, comprising particulates of 4,6-bis(dimethylamino)-2-(4-(4-(trifluoromethyl)benzamido)benzyl)pyrimidin-5-yl}acetic acid in an amorphous form, crystalline Form I or II, or a mixture thereof, and one or more pharmaceutically acceptable carriers or excipients.

Further provided is a method for treating, preventing, or ameliorating one or more symptoms of a CRTH2-mediated disorder or disease, which comprises administering particulates of {4,6-bis(dimethylamino)-2-(4-(4-(trifluoromethyl)benzamido)benzyl)-pyrimidin-5-yl}acetic acid in an amorphous form, crystalline Form I or II, or a mixture thereof.

Additionally, provided is a process for preparing particulates of 4,6-bis(dimethylamino)-2-(4-(4-(trifluoromethyl)benzamido)benzyl)pyrimidin-5-yl}acetic acid in an amorphous form, or crystalline Form I or II.

DETAILED DESCRIPTION

Figure 1:
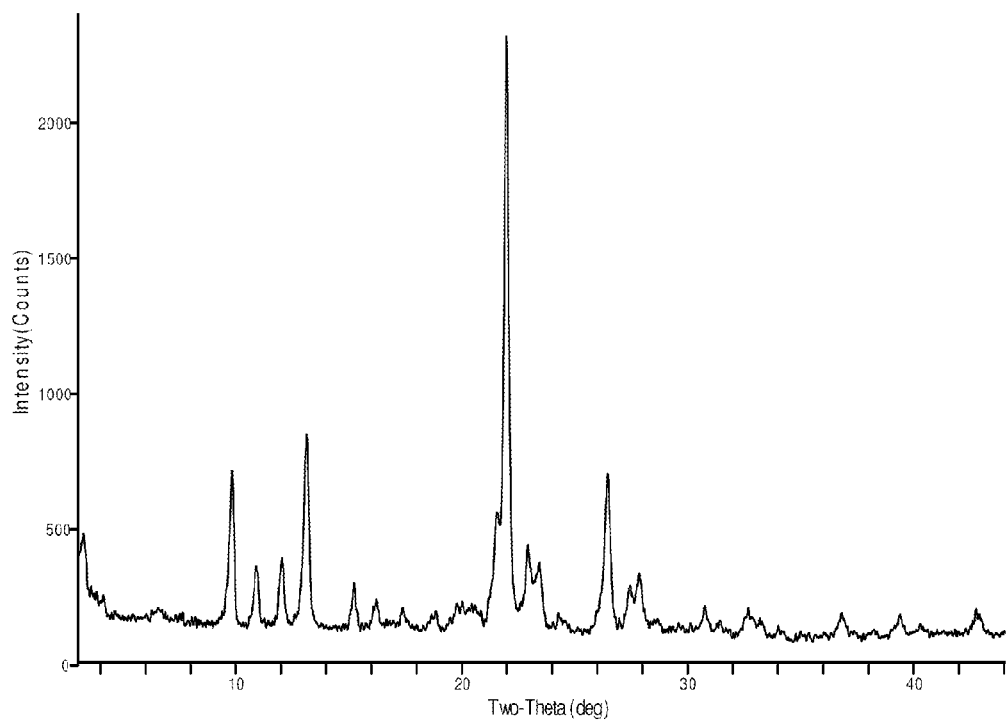
FIG. 1 depicts an X-ray powder (XRP) diffractogram of particulates of {4,6-bis(dimethyl-amino)-2-(4-(4-(trifluoromethyl)benzamido)benzyl)pyrimidin-5-yl}acetic acid in crystalline Form I.

To facilitate understanding of the disclosure set forth herein, a number of terms are defined below.

As used herein, the singular forms "a," "an," and "the" may refer to plural articles unless specifically stated otherwise. Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term herein, those in this section prevail unless stated otherwise.

The term "anti-solvent" refers to a liquid that is added to a solvent to reduce the solubility of a compound in that solvent, resulting in precipitation of the compound.

The term "subject" refers to an animal, including, but not limited to, a primate (e.g., human), cow, sheep, goat, horse, dog, cat, rabbit, rat, or mouse. Typically, the terms "subject" and "patient" are used interchangeably herein in reference, for example, to a mammalian subject, particularly a human subject.

The terms "treat," "treating" and "treatment" are meant to include alleviating or abrogating a disorder or disease, or one or more of the symptoms associated with the disorder or disease; or alleviating or eradicating the cause(s) of the disorder or disease itself.

The terms "prevent," "preventing" and "prevention" refer to a method of delaying or precluding the onset of a disease and/or its attendant symptoms, barring a subject from acquiring a disease or reducing a subject's risk of acquiring a disease.

The term "therapeutically effective amount" refers to the amount of a compound that, when administered, is sufficient to prevent development of, or alleviate to some extent, one or more of the symptoms of the condition or disorder being treated. The term "therapeutically effective amount" also refers to the amount of a compound that will elicit the biological or medical response of a tissue, system, animal, or human that is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenecity, or other problems or complications, commensurate with a reasonable benefit/risk ratio.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "CRTH2" refers to a CRTH2 receptor protein or variant thereof, which is capable of mediating a cellular response to $PGD_2$ in vitro or in vivo. CRTH2 variants include proteins substantially homologous to a native CRTH2, i.e., proteins having one or more naturally or non-naturally occurring amino acid deletions, insertions or substitutions (e.g., CRTH2 derivatives, homologs and fragments), as compared to the amino acid sequence of a native CRTH2. The amino acid sequence of a CRTH2 variant is at least about 80% identical, at least about 90% identical, or at least about 95% identical to a native CRTH2.

The term "other $PGD_2$ receptor" refers to a prostanoid receptor protein other than CRTH2, or variant thereof, which is capable of mediating a cellular response to $PGD_2$ in vivo or in vitro. "Other $PGD_2$ receptor" may be selective for $PGD_2$, e.g., DP, or other one or more other prostanoids. "Other $PGD_2$ receptor" variants include proteins substantially homologous to a corresponding native prostanoid receptor other than CRTH2, i.e., proteins having one or more naturally or non-naturally occurring amino acid deletions, insertions, or substitutions (e.g., derivatives, homologs, and fragments of a native prostanoid receptor other than CRTH2). The amino acid sequence of a native "other $PGD_2$ receptor" variants is at least about 80% identical, at least about 90% identical, or at least about 95% identical to the corresponding native "other $PGD_2$ receptor".

The term "CRTH2 antagonist" refers to a compound that, e.g., partially or totally blocks, decreases, prevents, inhibits, or downregulates CRTH2 activity and/or the activity of one or more other $PGD_2$ receptors. The term "CRTH2 antagonist" also refers to a compound that binds to, delays the activation of, inactivates, or desensitizes CRTH2 or one or more other $PGD_2$ receptors. A CRTH2 antagonist may act by interfering with the interaction of $PGD_2$ with CRTH2 or one or more other $PGD_2$ receptors.

The terms "CRTH2-mediated disorder or disease" and "a condition, disorder or disease mediated by CRTH2" refer to a condition, disorder, or disease characterized by inappropriate, e.g., less than or greater than normal, CRTH2 activity. Inappropriate CRTH2 functional activity might arise as the result of CRTH2 expression in cells which normally do not express CRTH2, increased CRTH2 expression or degree of intracellular activation, leading to, e.g., inflammatory and immune-related disorders or diseases; or decreased CRTH2 expression. A CRTH2-mediated condition, disorder or disease may be completely or partially mediated by inappropriate CRTH2 activity. In particularly, a CRTH2-mediated condition, disorder or disease is one in which modulation of CRTH2 or one or more other $PGD_2$ receptors results in some effect on the underlying condition or disorder, e.g., a CRTH2 antagonist or agonist results in some improvement in at least some of patients being treated.

The term "tapped bulk density" refers to bulk density under a densely filled state with the aid of tapping, such as dropping a container filled with a sample from a predetermined height in repetition to give a light impact on the bottom of the container. Tapped bulk density can be determined using, for example, Powder Tester PT-D (Hosokawa Micron Corporation, Osaka, Japan).

The term "uniformity coefficient" refers to a parameter that indicates the degree of uniformity of the particle size distribution of particulates, and is defined as a value obtained dividing the particle size at 60 percentile with the particle size at 10 percentile, which are obtained from a particle distribution curve. As the particles size distribution becomes more uniform, the uniformity coefficient approaches 1.

Particulates

Provided herein are particulates of {4,6-bis(dimethylamino)-2-(4-(4-(trifluoromethyl)benzamido)benzyl)pyrimidin-5-yl}acetic acid in an amorphous form, or crystalline Form I or II. The particulates of the acid of Formula I may be characterized using a number of methods known to a person skilled in the art, including single crystal X-ray diffraction, X-ray powder diffraction (XRPD), microscopy (e.g., scanning electron microscopy (SEM)), thermal analysis (e.g., differential scanning calorimetry (DSC), thermal gravimetric analysis (TGA), and hot-stage microscopy), and spectroscopy (e.g., infrared, Raman, solid-state nuclear magnetic resonance). The particle size and size distribution may be determined by conventional methods, such as laser light scattering technique. The purity of the particulates of the acid of Formula I may be determined by standard analytical methods, such as thin layer chromatography (TLC), gel electrophoresis, gas chromatography, high performance liquid chromatography (HPLC), and mass spectrometry (MS).

Figure 2:
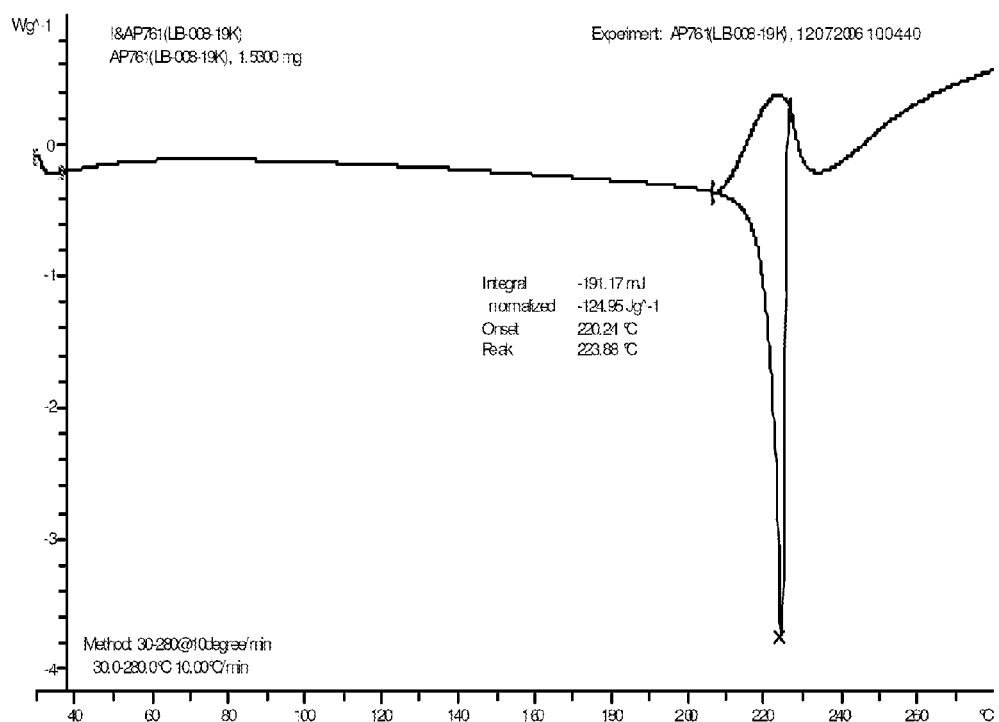
FIG. 2 depicts a differential scanning calorimetric (DSC) thermogram of the particulates of the acid of Formula I in Form I.
Figure 4A:
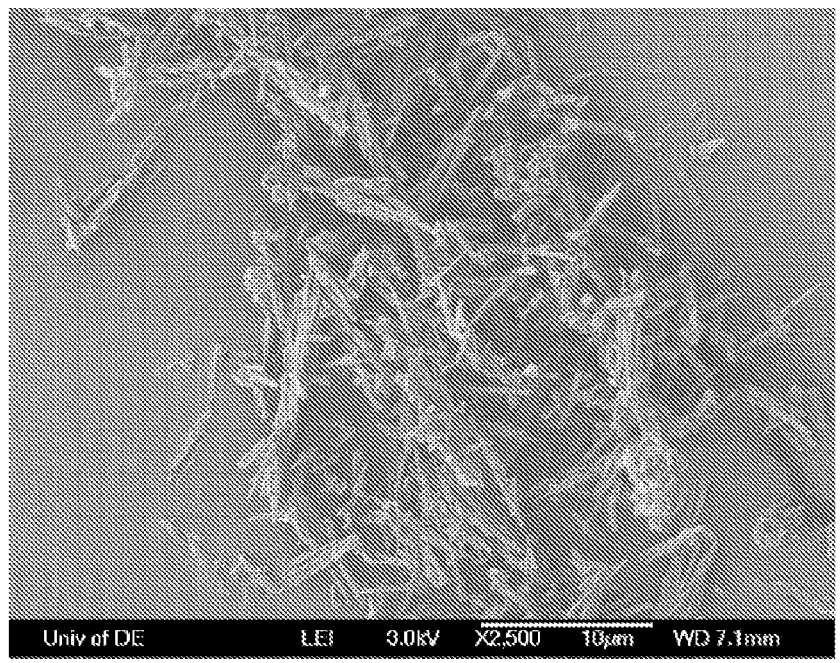
FIG. 4 depict scanning electron microscopic (SEM) photographs of the particulates of the acid of Formula I in Form I at magnification of 2,500 (A); 5,000 (B); and 10,000 (C).
Figure 4B:
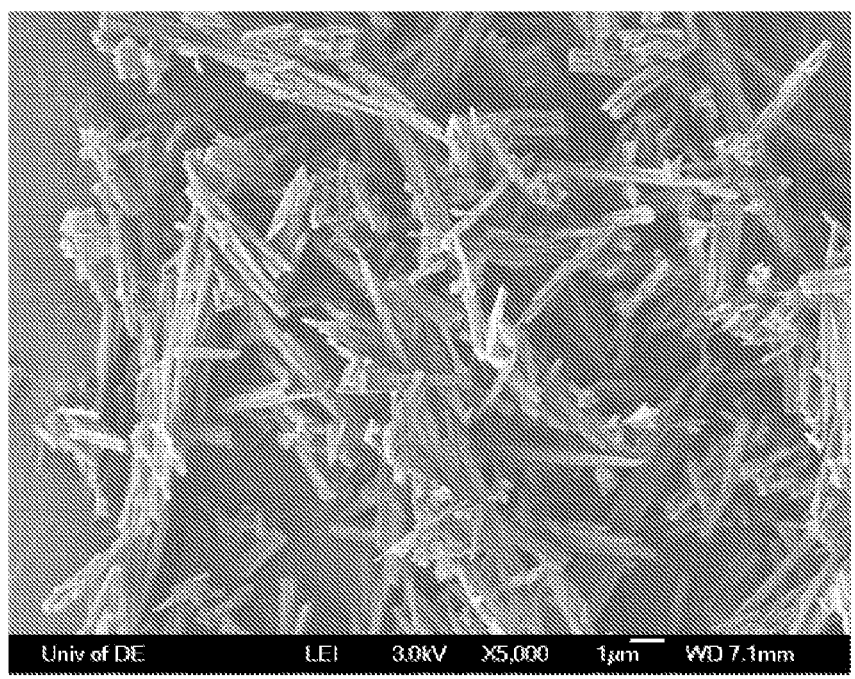
Figure 4C:
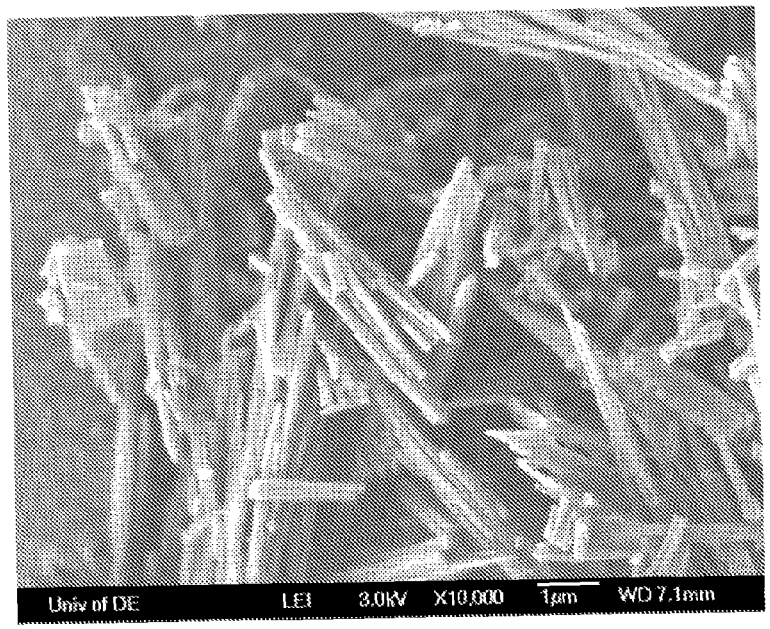

In one embodiment, particulates of {4,6-bis(dimethylamino)-2-(4-(4-(trifluoromethyl)benzamido)benzyl)pyrimidin-5-yl}acetic acid are in crystalline Form I. In one embodiment, the particulates of Form I have an X-ray powder diffraction pattern substantially as shown in FIG. 1. In another embodiment, the particulates of Form I have characteristic XRP diffraction peaks at two-theta angles of approximately 9.8, 13.1, 22.0, and 26.4°. In yet another embodiment, the particulates of Form I have characteristic XRP diffraction a peak at a two-theta angle of approximately 9.8, 13.1, 22.0, or 26.4°. In yet another embodiment, the particulates of Form I have characteristic XRP diffraction a peak at a two-theta angle of approximately 22.0°. In yet another embodiment, the particulates of Form I have a differential scanning calorimetric thermogram substantially as shown in FIG. 2. In yet another embodiment, the particulates of Form I have a DSC thermogram with an endotherm at a peak temperature of about 224° C. and an onset temperature of about 220° C. In yet another embodiment, the crystal habit of the particulates of Form I is substantially acicular (FIG. 4). In still another embodiment, the particulates of Form I have an aqueous solubility of about 3 µg/mL at room temperature.

In one embodiment, the particulates of Form I may have an average particle size ranging from about 0.1 to about 150 µm, from about 0.5 to about 100 µm, from about 1 to about 50 µm, from about 1 to about 25 µm, from about 1 to about 20 µm, from about 1 to about 10 µm, from about 2 to about 10 µm, or from about 2 to about 7.5 µm. In another embodiment, the particulates of Form I may have a uniform particle size distribution, as measured by a uniformity coefficient, ranging from about 1 to about 20, from about 1 to about 10, from about 2 to about 5, or from about 3 to about 4. In still another embodiment, the particulates of Form I may have a tapped bulk density, ranging from about 0.1 to about 1.0, from about 0.15 to about 0.8, from about 0.2 to about 0.6, from about 0.25 to about 0.5, or from about 0.3 to about 0.4 g/mL.

The particulates with such particle properties may be prepared directly by the process of preparation described herein. Alternatively, the particulates of such sizes may also be prepared using any conventional particle processing methods, such as milling, micronization, or granulation. The particulates of Form I provided herein are suitable for direct manufacture of the acid of Formula I as therapeutic products, thus simplifying the manufacturing process and eliminating the risks associated with conventional particle processing methods, such as undesired polymorph conversion.

In certain embodiments, the particulates of the acid of Formula I in Form I may contain no less than about 95%, no less than about 97%, no less than about 98%, no less than about 99%, or no less than about 99.5% by weight of the acid of Formula I. The particulates may also contain no less than about 90%, no less than about 95%, no less than about 98%, no less than about 99%, or no less than about 99.5% by weight of the particulates in Form I.

In certain embodiments, the particulates of the acid of Formula I in Form I may have a residual organic solvent content of no greater than about 5%, no greater than about 2%, no greater than about 1%, no greater than about 0.9%, no greater than about 0.8%, no greater than about 0.7%, no greater than about 0.6%, no greater than about 0.5%, no greater than about 0.4%, no greater than about 0.3%, no greater than about 0.2%, no greater than about 0.1%, no greater than about 0.05%, or no greater than about 0.01% by weight.

In certain embodiments, the particulates of the acid of Formula I in Form I may have a residual methanol content of no greater than about 100,000 ppm, no greater than about 10,000 ppm, no greater than about 5,000 ppm, no greater than about 4,000 ppm, no greater than about 3,000 ppm, no greater than about 2,000 ppm, no greater than about 1,000 ppm, no greater than about 500 ppm, or no greater than about 100 ppm.

Figure 6:
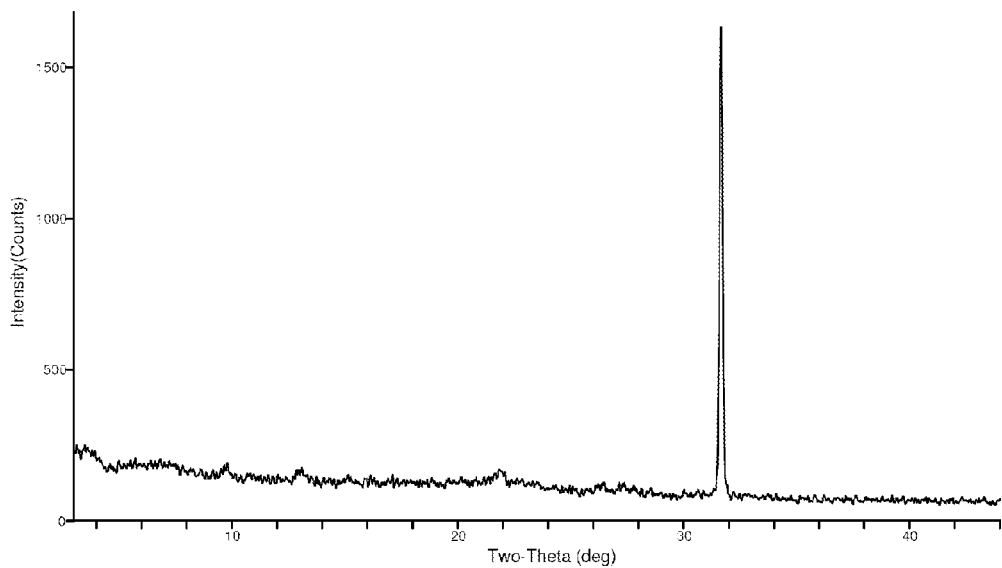
FIG. 6 depicts an XRP diffractogram of particulates of the acid of Formula I in Form II.
Figure 7A:
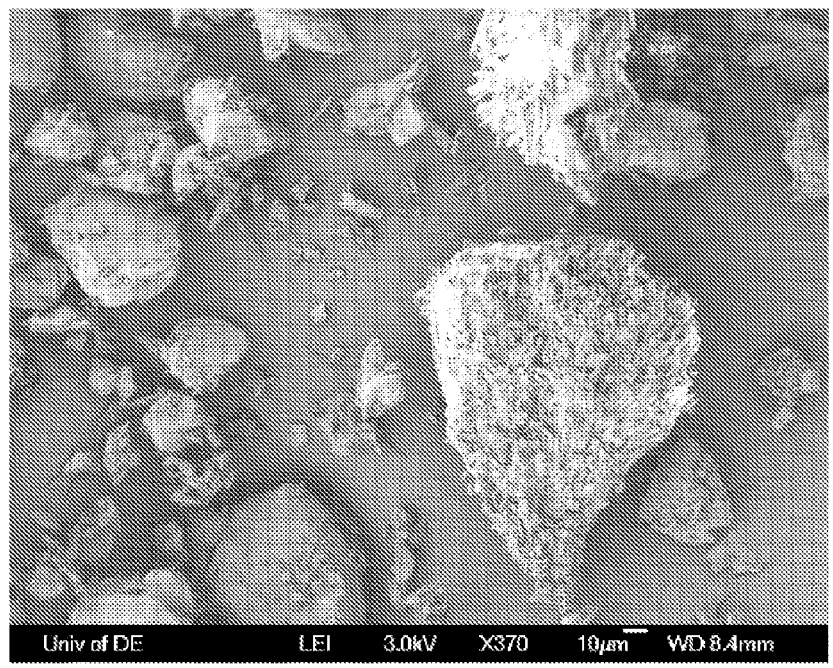
FIG. 7 depict SEM photographs of the particulates of the acid of Formula I in Form II at magnification of 370 (A); 2,000 (B); 5,500 (C); and 10,000 (D).
Figure 7B:
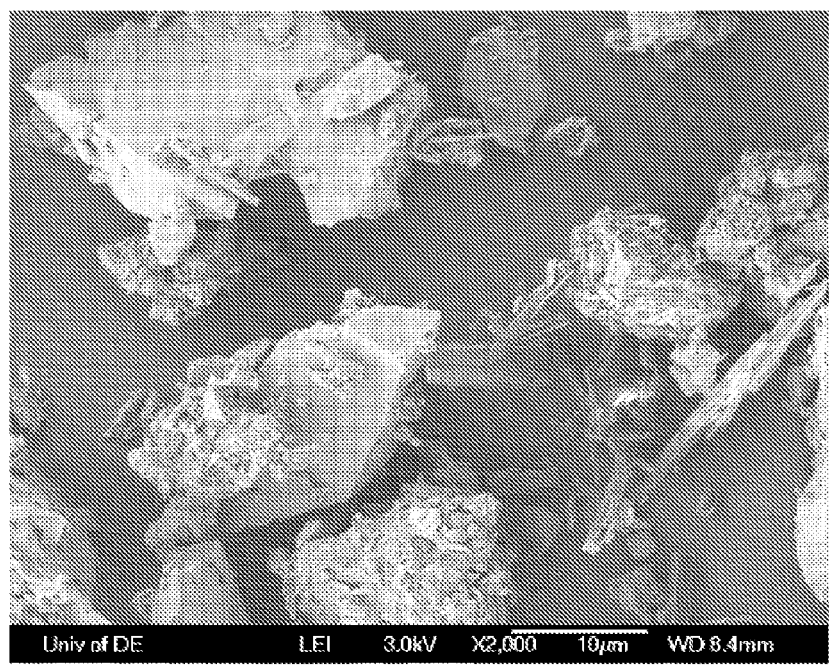
Figure 7C:
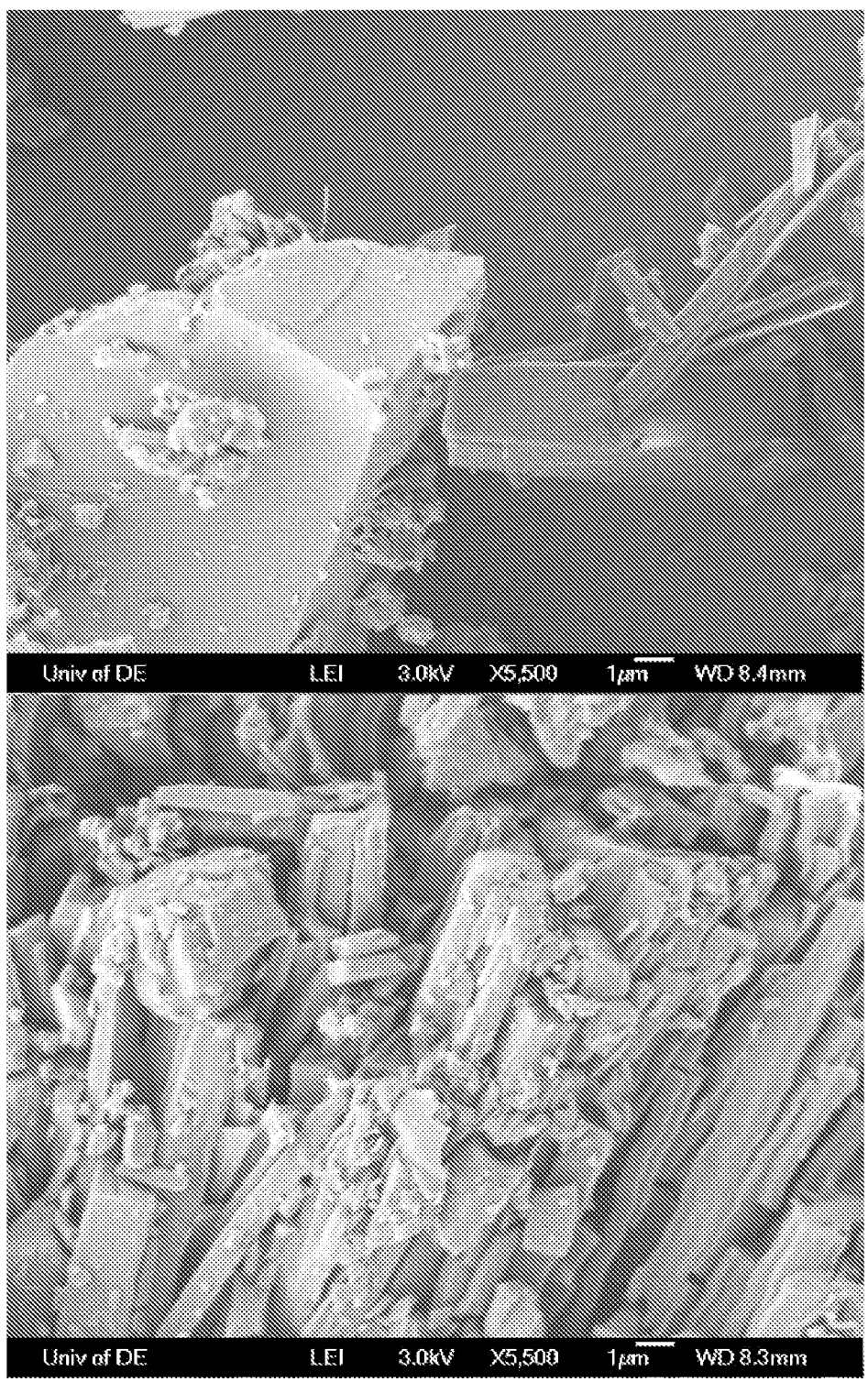
Figure 7D:
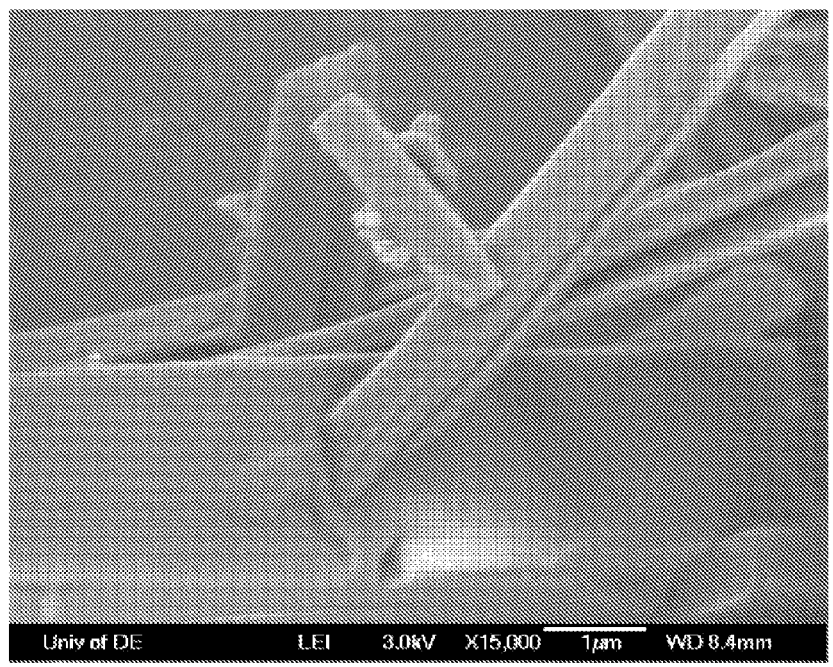

In another embodiment, the particulates of {4,6-bis(dimethylamino)-2-(4-(4-(trifluoromethyl)benzamido)benzyl)pyrimidin-5-yl}acetic acid are in crystalline Form II. The particulates of Form II have an X-ray powder diffraction pattern substantially as shown in FIG. 6. The particulates of Form I have a characteristic XRP diffraction peak at a two-theta angle of approximately 31.7°.

In one embodiment, the particulates of Form II may an average particle size ranging from about 0.1 to about 150 µm, from about 0.5 to about 100 µm, from about 1 to about 50 µm, from about 1 to about 25 µm, from about 1 to about 20 µm, from about 1 to about 10 µm, from about 1 to about 5 µm, or from about 2 to about 5 µm. In another embodiment, the particulates of Form II may have a uniform particle size distribution, as measured by a uniformity coefficient, ranging from about 1 to about 20, from about 1 to about 10, from about 2 to about 5, or from about 3 to about 4. In yet another embodiment, the particulates of Form II may have a tapped bulk density, ranging from about 0.1 to about 1.0, from about 0.15 to about 0.8, from about 0.2 to about 0.6, from about 0.25 to about 0.5, or from about 0.3 to about 0.4 g/mL.

The particulates of such particle properties may be prepared directly by the process of preparation described herein. Alternatively, the particulates of such sizes may also be prepared using any conventional methods, such as milling, micronization, or granulation.

In certain embodiments, the particulates of the acid of Formula I in Form II may contain no less than about 95%, no less than about 97%, no less than about 98%, no less than about 99%, or no less than about 99.5% by weight of the acid of the acid of Formula I. The particulates may also contain no less than about 90%, no less than about 95%, no less than about 98%, no less than about 99%, or no less than about 99.5% by weight of the particulates in Form II.

In certain embodiments, the particulates of the acid of Formula I in Form II may have a residual organic solvent content of no greater than about 5%, no greater than about 2%, no greater than about 1%, no greater than about 0.9%, no greater than about 0.8%, no greater than about 0.7%, no greater than about 0.6%, no greater than about 0.5%, no greater than about 0.4%, no greater than about 0.3%, no greater than about 0.2%, no greater than about 0.1%, no greater than about 0.05%, or no greater than about 0.01% by weight.

Figure 9:
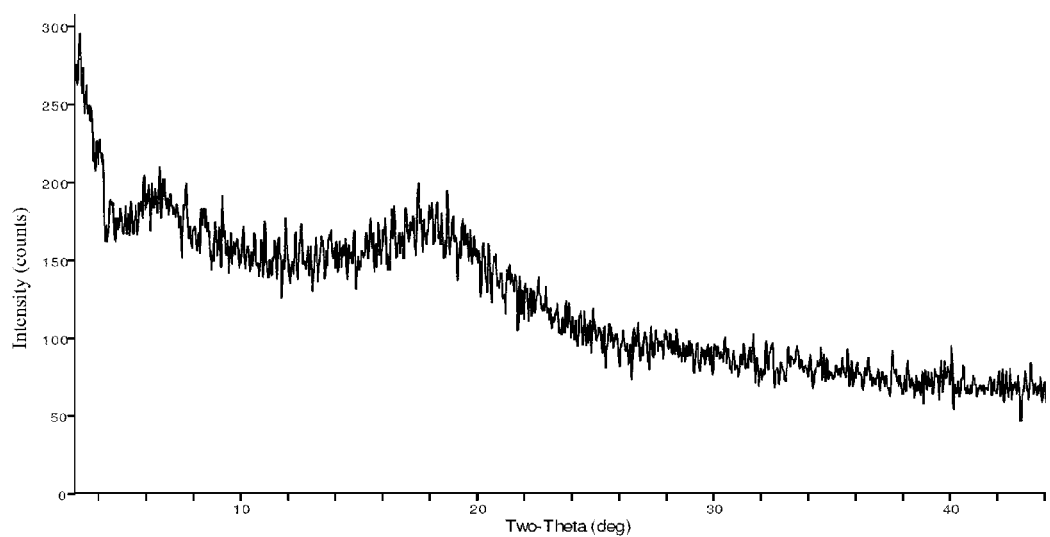
FIG. 9 depicts an XRP diffractogram of the acid of Formula I in an amorphous form.
Figure 10:
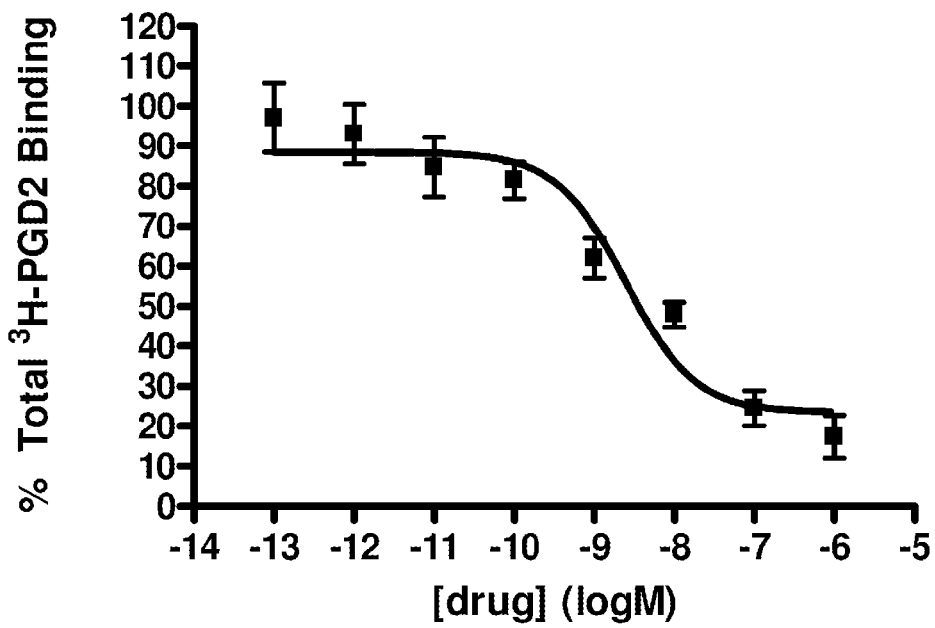
FIG. 10 depicts a dose response curve for {4,6-bis(dimethylamino)-2-(4-(4-(trifluoromethyl)-benzamido)benzyl)-pyrimidin-5-yl}acetic acid of Formula I in a competitive radioligand binding assay using CRTH2-transfected cells.
Figure 11:
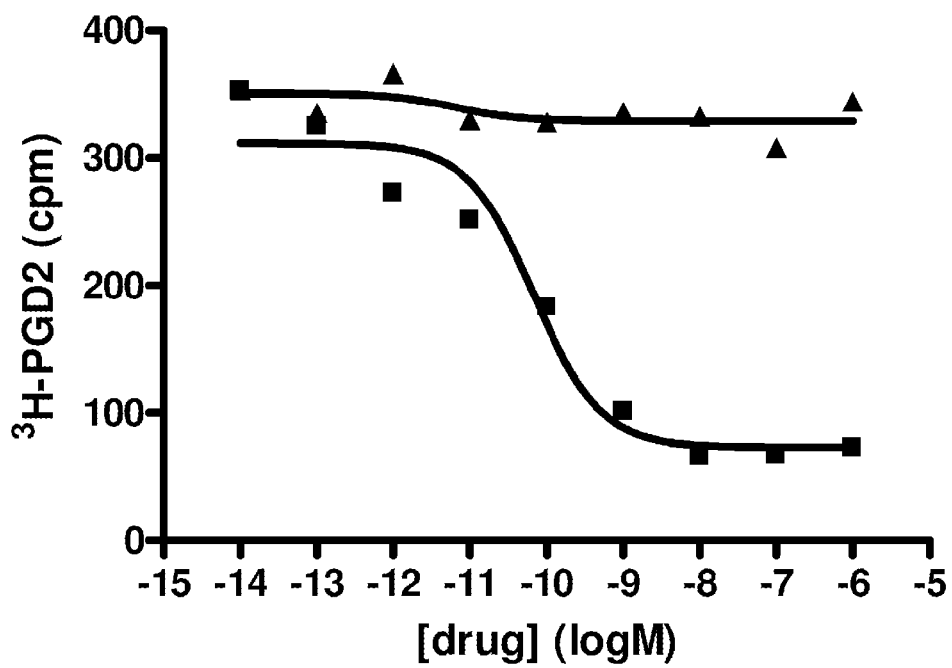
FIG. 11 depicts a dose response curve for {4,6-bis(dimethylamino)-2-(4-(4-(trifluoromethyl)-benzamido)benzyl)-pyrimidin-5-yl}acetic acid of Formula I (▲), along with a DP1-selective antagonist BWA 868C (■) for comparison, in a competitive radioligand binding assay using DP1-transfected cells.

In yet another embodiment, the particulates of {4,6-bis(dimethylamino)-2-(4-(4-(trifluoromethyl)benzamido)benzyl)pyrimidin-5-yl}acetic acid are amorphous. The amorphous particulates have an X-ray powder diffraction pattern substantially as shown in FIG. 9, which lacks the characteristic XRP diffraction peaks for the particulates of Form I and/or Form II. In one embodiment, the amorphous particulates may contain no less than about 95%, no less than about 97%, no less than about 98%, no less than about 99%, or no less than about 99.5% by weight of the acid of the acid of Formula I. In another embodiment, the particulates may also contain no less than about 90%, no less than about 95%, no less than about 98%, no less than about 99%, or no less than about 99.5% by weight of the amorphous particulates.

In certain embodiments, the amorphous particulates of the acid of Formula I may have a residual organic solvent content of no greater than about 5%, no greater than about 2%, no greater than about 1%, no greater than about 0.9%, no greater than about 0.8%, no greater than about 0.7%, no greater than about 0.6%, no greater than about 0.5%, no greater than about 0.4%, no greater than about 0.3%, no greater than about 0.2%, no greater than about 0.1%, no greater than about 0.05%, or no greater than about 0.01% by weight.

It should be understood that the numerical values of the peaks of the X-ray powder diffraction patterns may vary slightly from one machine to another or from one sample to another, and so the values quoted are not to be construed as absolute, but with an allowable variability, such as 0.1°, which is recommended in the United State Pharmacopeia (pages: 387-389, 2007).

Process of Preparation

Also provided are processes for preparing particulates of the acid of Formula I in an amorphous form, or crystalline Form I or II. The processes comprise the step of contacting the acid of Formula I with a solvent, in which the particulates of the acid of Formula I in an amorphous form, or crystalline Form I or II may be formed from a solution or converted from one solid form to another. The process may further comprise an isolation step, in which the particulates may be isolated by a conventional method, such as filtration and centrifugation, followed by washing with a solvent and then drying (e.g., vacuum oven drying, air drying, or desicator drying).

Suitable solvents for use in preparing the particulates in an amorphous form, or crystalline Form I or II include, but are not limited to, hydrocarbons, including petroleum ether, pentane, hexane(s), heptane, octane, isooctane, cyclopentane, cyclohexane, methylcyclohexane, benzene, toluene, xylene, tetralin, and cumene; chlorinated hydrocarbons, including dichloromethane (DCM), 1,2-dichloroethane, 1,1-dichloroethene, 1,2-dichloroethene, chloroform, trichloroethane, trichloroethene, carbon tetrachloride, chlorobenzene, and trifluoromethylbenzene; alcohols, including methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, and ethyleneglycol; ethers, including diethyl ether, diisopropyl ether, methyl t-butyl ether (MTBE), diphenyl ether, 1,2-dimethoxyethane, bi(2-methoxyethyl) ether, 1,1-dimethoxymethane, 2,2-dimethoxypropane, and anisole; ketones, including acetone, butanone, methyl ethyl ketone (MEK), methyl isopropyl ketone, methyl butyl ketone, and methyl isobutyl ketone (MIBK); esters, including methyl acetate, ethyl formate, ethyl acetate, propyl acetate, isopropyl acetate, isobutyl acetate, and butyl acetate; carbonates, including ethylene carbonate and propylene carbonate; amides, including formamide, N,N-dimethylformamide (DMF), and N,N-dimethylacetamide; nitriles, including acetonitrile (ACN); sulfoxides, such as dimethyl sulfoxide (DMSO); sulfones, such sulfolane; nitro compounds, such as nitromethane and nitrobenzene; heterocycles, such as N-methyl pyrrolindone, 2-methyl tetrahydrofuran, tetrahydrofuran (THF), dioxane, and pyridine; carboxylic acids, such as acetic acid, trichloroacetic acid, and trifluoroacetic acid; phosphoramides, such as hexamethylphosphoramide; carbon sulfide; water; and mixtures thereof.

The particulates of the acid of Formula I in crystalline Form I can be prepared from a solution or slurry of the acid of Formula I in a solvent using conventional methods, including, but not limited to, cooling, chilling, solvent evaporation, or addition of an anti-solvent.

In one embodiment, the process for preparing the particulates of Form I comprises the steps of (a) preparing a solution of the acid of Formula I in a solvent at a first temperature; and (b) generating the particulates of Form I at a second temperature. To accelerate the formation of the particulates of Form I, the process may also comprise an seeding step by seeding the solution with crystals of Form I, prior to or during step (b). The process may further comprise an isolation step as described herein.

The solution can be prepared from any forms of the acid of Formula I, including, but not limited to, oil, semisolids, solids (such as an amorphous form, or Form I or II), or mixtures thereof. The solution of step (a) may be prepared as a saturated or nearly saturated solution at the first temperature. The saturated or nearly saturated solution can be prepared by dissolving a sufficient amount of the acid of Formula I in the solvent at a temperature that is higher than the first temperature, such that, when the solution is allowed to cool to the first temperature, a saturated or nearly saturated solution is obtained. The sufficient amount of the acid of Formula I can be estimated based on the solubility of the particulates of Form I in the solvent at the first temperature, which can be determined using a method known to a person skilled in the art.

The first temperature may range from room temperature to about the boiling point of the solvent, e.g., from about 20 to about 200° C., from about 20 to about 150° C., or from about 20 to about 100° C. The second temperature may range from −100 to 100° C., from about −50 to about 50° C., from about −10 to about 30° C., 20 to about 200° C., from about 20 to about 150° C., or from about 20 to about 100° C. The first temperature may be higher or lower than, or the same as the second temperature. To maximize the yield and the efficiency of the process, the second temperature is normally set to be lower than the first temperature.

In one embodiment, the particulates of Form I are formed by evaporating the solvent from the solution at the second temperature. The solvent evaporation can be facilitated by applying heat and/or vacuum to the solution. In one embodiment, the solvent is acetonitrile, dichloromethane, DMF, 1,4-dioxane, methanol, 2-methoxyethanol, MIBK, acetone, 1-butanol, MTBE, DMSO, ethanol, ethyl acetate, isobutyl acetate, isopropyl acetate, 1-propanol, IPA, MEK, THF, or a mixture thereof.

In another embodiment, the particulates of Form I are formed by cooling the solution to the second temperature. In this case, the second temperature is set to be lower than the first temperature. In one embodiment, the solvent is DMF, 1,4-dioxane, methanol, 2-methoxyethanol, 1-butanol, 1-propanol, IPA, MEK, THF, or a mixture thereof.

In yet another embodiment, the particulates of Form I are formed by adding an anti-solvent to the solution at a second temperature.

Suitable anti-solvents include, but are not limited to, hydrocarbons, including petroleum ether, pentane, hexane(s), heptane, octane, isooctane, cyclopentane, cyclohexane, methylcyclohexane, benzene, toluene, xylene, tetralin, and cumene; chlorinated hydrocarbons, including dichloromethane (DCM), 1,2-dichloroethane, 1,1-dichloroethene, 1,2-dichloroethene, chloroform, trichloroethane, trichloroethene, carbon tetrachloride, chlorobenzene, and trifluoromethylbenzene; alcohols, including isopropanol (IPA), 1-propanol, 1-butanol, 2-butanol, t-butanol, 3-methyl-1-butanol, 1-pentanol, 2-ethoxyethanol, and ethyleneglycol; ethers, including diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, and anisole; ketones, including butanone, methyl isopropyl ketone, methyl butyl ketone, and methyl isobutyl ketone (MIBK); esters, including methyl acetate, ethyl formate, ethyl acetate, propyl acetate, isopropyl acetate, isobutyl acetate, and butyl acetate; carbonates, including ethylene carbonate and propylene carbonate; nitro compounds, including nitromethane and nitrobenzene; heterocycles; carbon sulfide; water; and mixtures thereof.

When two solvents are used as a solvent/anti-solvent pair, the acid of Formula I has a higher solubility in the solvent than in the anti-solvent. Optionally, the solvent and the anti-solvent in a solvent/anti-solvent pair are at least partially miscible. In one embodiment, the solvent is THF, methoxyethanol, DMSO, DMF, or a mixture thereof; and the anti-solvent is hexane(s), MTBE, toluene, water, or a mixture thereof. In another embodiment, the solvent/anti-solvent pair is THF/hexane, THF/water, DMF/MTBE, or DMF/water.

In yet another embodiment, the particulates of Form I are formed by adding the solution to an anti-solvent at the second temperature. In one embodiment, the solvent is THF, methoxyethanol, DMSO, DMF, or a mixture thereof; and the anti-solvent is hexane(s), MTBE, toluene, isopropyl acetate, water, or a mixture thereof. In another embodiment, the solvent/anti-solvent pair is THF/hexane, THF/water, 2-methoxyethanol/hexane, DMSO/water, or DMF/water.

In another embodiment, the process for preparing the particulates of Form I comprises the steps of (a) preparing a slurry of the acid of Formula I in a solvent at a first temperature; and (b) generating the particulates of Form I by exposing the slurry to a second temperature. The slurry can be prepared from any forms of the acid of Formula I, including, but not limited to, oil, semisolids, solids (such as an amorphous form, or Form I or II), or mixtures thereof. The process may further comprise a seeding step and/or an isolation step, as described herein.

The first and second temperatures and the solvent are as defined herein. In one embodiment, the solvent is acetonitrile, chloroform, dichloromethane, DMF, 1,4-dioxane, methanol, 2-methoxyethanol, MIBK, toluene, hexane(s), acetone, 1-butanol, MTBE, DMSO, ethanol, ethyl acetate, ethyl formate, heptane, isobutyl acetate, isopropyl acetate, 1-propanol, IPA, MEK, THF, water, or a mixture thereof.

In yet another embodiment, the process for preparing the particulates of Form I comprises the steps of (a) preparing a solution of the acid of Formula I in a solvent at a first temperature; (b) forming a slurring by cooling the solution to a second temperature; and (c) generating the particulates of Form I by exposing the slurry to one or more heating and cooling cycles. The process may further comprise a seeding step and/or an isolation step, as described herein.

The first and second temperatures and the solvent are as defined herein. In one embodiment, the solvent is acetonitrile, 1,4-dioxane, 2-methoxyethanol, MIBK, acetone, 1-butanol, ethanol, 1-propanol, IPA, MEK, THF, water/THF (3:7, v/v), or a mixture thereof. The heating and cooling cycle may be performed in a temperature range between about −50 to about 120° C., about −50 to about 100° C., about −20 to about 80° C., about 0 to about 80° C., about 10 to about 80° C., about 20 to about 80° C., about 20 to about 60° C., or about 20 to about 50° C.

The particulates of the acid of Formula I in crystalline Form II can be prepared from a solution or slurry of the acid of Formula I in a solvent using conventional methods, including, but not limited to, cooling, chilling, solvent evaporation, or addition of an anti-solvent.

In one embodiment, the process for preparing the particulates of Form II comprises the steps of (a) preparing a solution of the acid of Formula I in a solvent at a first temperature; and (b) generating the particulates of Form II at a second temperature. To accelerate the formation of the particulates of Form II, the process may also comprise a seeding step by seeding the solution with crystals of Form II, prior to or during step (b). The process may further comprise an isolation step as described herein.

The solution can be prepared from any forms of the acid of Formula I, including, but not limited to, oil, semisolids, solids (such as an amorphous form, or Form I or II), or mixtures thereof. The solution of step (a) may be prepared as a saturated or nearly saturated solution at the first temperature. The saturated or nearly saturated solution may be prepared by dissolving a sufficient amount of the acid of Formula I in the solvent at a temperature that is higher than the first temperature, such that, when the solution is allowed to cool to the first temperature, a saturated or nearly saturated solution is obtained. The sufficient amount of the acid of Formula I can be estimated based on the solubility of the particulates of Form II in the solvent at the first temperature, which can be determined using a method known to a person skilled in the art.

In one embodiment, the particulates of Form II are formed by evaporating the solvent from the solution at the second temperature. The solvent evaporation can be facilitated by applying heat and/or vacuum to the solution. In one embodiment, the solvent is DMF, 1,4-dioxane, methanol, 2-methoxyethanol, 1-butanol, 1-propanol, IPA, MEK, THF, or a mixture thereof.

In another embodiment, the particulates of Form II are formed by cooling the solution to the second temperature.

In yet another embodiment, the particulates of Form II are formed by adding an anti-solvent to the solution at the second temperature. In one embodiment, the solvent is THF, methoxyethanol, DMSO, DMF, or a mixture thereof; and the anti-solvent is hexane(s), MTBE, toluene, water, or a mixture thereof.

In yet another embodiment, the particulates of Form II are formed by adding the solution to an anti-solvent at the second temperature. In one embodiment, the solvent is THF, methoxyethanol, DMSO, DMF, and mixtures thereof; and the anti-solvent is hexane(s), MTBE, toluene, water, and mixtures thereof. In another embodiment, the solvent/anti-solvent pair is DMF/MTBE.

In another embodiment, the process for preparing the particulates of Form II comprises the steps of (a) preparing a slurry of the acid of Formula I in a solvent at a first temperature; and (b) generating the particulates of Form II by exposing the slurry to a second temperature. The slurry can be prepared from any forms of the acid of Formula I, including, but not limited to, oil, semisolids, solids (such as an amorphous form, or Form I or II), or mixtures thereof. The process may further comprise a seeding step and/or an isolation step, as described herein.

The first and second temperatures and the solvent are as defined herein. In one embodiment, the solvent is acetonitrile, chloroform, dichloromethane, DMF, 1,4-dioxane, methanol, 2-methoxyethanol, MIBK, toluene, hexane(s), acetone, 1-butanol, MTBE, DMSO, ethanol, ethyl acetate, ethyl formate, heptane, isobutyl acetate, isopropyl acetate, 1-propanol, IPA, MEK, THF, water, or a mixture thereof.

The amorphous particulates of the acid of Formula I can be prepared from a solution or slurry of the acid of Formula I in a solvent using conventional methods, including, but not limited to, cooling, chilling, solvent evaporation, or addition of an anti-solvent.

In one embodiment, the process for preparing the amorphous particulates of the acid of Formula I comprises the steps of (a) preparing a solution of the acid of Formula I in a solvent at a first temperature; and (b) generating the amorphous particulates at a second temperature. The process may also comprise an isolation step as described herein.

The solution can be prepared from any forms of the acid of Formula I, including, but not limited to, oil, semisolids, solids (such as an amorphous form, or Form I or II), or mixtures thereof. The solution of step (a) may be prepared as a saturated or nearly saturated solution at the first temperature. The saturated or nearly saturated solution may be prepared by dissolving a sufficient amount of the acid of Formula I in the solvent at a temperature that is higher than the first temperature, such that, when the solution is allowed to cool to the first temperature, a saturated or nearly saturated solution is obtained. The sufficient amount of the acid of Formula I can be estimated based on the solubility of the amorphous particulates in the solvent at the first temperature, which can be determined using a method known to a person skilled in the art.

In one embodiment, the amorphous particulates are formed by evaporating the solvent from the solution at the second temperature. The solvent evaporation can be facilitated by applying heat and/or vacuum to the solution. In one embodiment, the solvent is ethyl formate, isobutyl acetate, MTBE, or a mixture thereof.

In another embodiment, the amorphous particulates are formed by cooling the solution to the second temperature. In one embodiment, the solvent is MEK.

In yet another embodiment, the amorphous particulates are formed by adding an anti-solvent to the solution at the second temperature. In one embodiment, the solvent is THF, methoxyethanol, DMSO, DMF, or a mixture thereof; and the anti-solvent is hexane(s), MTBE, toluene, water, or a mixture thereof. In another embodiment, the solvent/anti-solvent pair is THF/hexane or DMSO/water.

In yet another embodiment, the amorphous particulates are formed by adding the solution to an anti-solvent at a second temperature. In one embodiment, the solvent is THF, methoxyethanol, DMSO, DMF, or a mixture thereof; and the anti-solvent is hexane(s), MTBE, toluene, water, or a mixture thereof. In another embodiment, the solvent/anti-solvent pair is THF/hexane or DMSO/water.

In yet another embodiment, the process for preparing the amorphous particulates of the acid of Formula I comprises the steps of (a) preparing a slurry of the acid of Formula I in a solvent at a first temperature; and (b) generating the amorphous particulates through phase conversion at a second temperature. The slurry can be prepared from any forms of the acid of Formula I, including, but not limited to, oil, semisolids, solids (such as an amorphous form, or Form I or II), or mixtures thereof. The first and second temperatures and the solvent are as defined herein. In one embodiment, the solvent is chloroform, hexane(s), MTBE, ethyl formate, heptane, IPA, water, or a mixture thereof.

Other particulate forming methods may also be applicable for preparing particulates of the acid of Formula I in an amorphous form, or crystalline Form I or II, including spray drying, roller drying, lyophilization, and melt crystallization.

Pharmaceutical Compositions

Also provided is a pharmaceutical composition which comprises particulates of {4,6-bis(dimethylamino)-2-(4-(4-(trifluoromethyl)benzamido)-benzyl)pyrimidin-5-yl}acetic acid in an amorphous form, or crystalline Form I or II, or a pharmaceutically acceptable hydrate or solvate thereof, as an active pharmaceutical ingredient, in combination with one or more pharmaceutically acceptable carriers or excipients. The choice of excipient, to a large extent, depends on factors, such as the particular mode of administration, the effect of the excipient on the solubility and stability of the active ingredient, and the nature of the dosage form.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampouls, syringes, and individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The particulates of the acid of Formula I provided herein may be administered alone, or in combination with one or more other compounds provided herein, one or more other active ingredients. The pharmaceutical compositions provided herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy, supra; Modified-Release Drug Deliver Technology*, Rathbone et al., Eds., Drugs and the Pharmaceutical Science, Marcel Dekker, Inc.: New York, N.Y., 2002; Vol. 126).

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein may be provided in solid, semisolid, or liquid dosage forms for oral administration. As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of nonaqueous liquids utilized in emulsions include mineral oil and cottonseed oil. Organic acids include citric and tartaric acid. Sources of carbon dioxide include sodium bicarbonate and sodium carbonate.

It should be understand that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Miccellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained-, pulsed-, controlled, targeted-, and programmed-release forms.

The pharmaceutical compositions provided herein may be co-formulated with other active ingredients which do not impair the desired therapeutic action, or with substances that supplement the desired action, such as antacids, proton pump inhibitors, and $H_2$-receptor antagonists.

B. Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl p-hydroxybenzates, thimerosal, benzalkonium chloride, benzethonium chloride, methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including alpha-cyclodextrin, beta-cyclodextrin, hydroxypropyl-beta-cyclodextrin, sulfobutylether-beta-cyclodextrin, and sulfobutylether 7-beta-cyclodextrin (CAPTISOL®, CyDex, Lenexa, Kans.).

The pharmaceutical compositions provided herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained-, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein may be administered topically to the skin, orifices, or mucosa. The topical administration, as used herein, include (intra)dermal, conjuctival, intracorneal, intraocular, ophthalmic, auricular, transdermal, nasal, vaginal, urethral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryopretectants, lyoprotectants, thickening agents, and inert gases.

The pharmaceutical compositions may also be administered topically by electroporation, iontophoresis, phonophoresis, sonophoresis and microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon bases, including such as lard, benzoinated lard, olive oil, cottonseed oil, and other oils, white petrolatum; emulsifiable or absorption bases, such as hydrophilic petrolatum, hydroxystearin sulfate, and anhydrous lanolin; water-removable bases, such as hydrophilic ointment; water-soluble ointment bases, including polyethylene glycols of varying molecular weight; emulsion bases, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, Carbopol®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as 50 micrometers or less, or 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

D. Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile- or pulsed-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form may be fabricated using a matrix controlled release device known to those skilled in the art (see, Takada et al. in "Encyclopedia of Controlled Drug Delivery," Vol. 2, Mathiowitz ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In another embodiment, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients in the compositions.

The pharmaceutical compositions provided herein in a modified release dosage form may be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-tolunesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiment, the pharmaceutical compositions provided herein are formulated as ESC controlled-release dosage form, which comprises an osmotic membrane that coats a core comprising the active ingredient(s), hydroxylethyl cellulose, and other pharmaceutically acceptable excipients.

3. Multiparticulate Controlled Release Devices

The pharmaceutical compositions provided herein in a modified release dosage form may be fabricated a multiparticulate controlled release device, which comprises a multiplicity of particles, granules, or pellets, ranging from about 10 µm to about 3 mm, about 50 µm to about 2.5 mm, or from about 100 µm to 1 mm in diameter. Such multiparticulates may be made by the processes know to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided is a method of treating, preventing, or ameliorating one or more symptoms of a disorder or disease associated with CRTH2 and/or one or more other $PGD_2$ receptors by administering to a subject having or being suspected to have such a condition or disease, a therapeutically effective amount of particulates of {4,6-bis(dimethylamino)-2-(4-(4-(trifluoromethyl)benzamido)-benzyl)pyrimidin-5-yl}acetic acid in an amorphous form, or crystalline Form I or II.

In another embodiments, provided is a method of treating, preventing, or ameliorating one or more symptoms of a disease or disorder responsive to modulation of CRTH2 and/or one or more other $PGD_2$ receptors, comprising administering to a subject having or being suspected to have such a condition or disease, a therapeutically effective amount of particulates of {4,6-bis(dimethylamino)-2-(4-(4-(trifluoromethyl)benzamido)-benzyl)pyrimidin-5-yl}acetic acid in an amorphous form, or crystalline Form I or II.

In yet another embodiment, provided is a method of treating, preventing, or ameliorating one or more symptoms of a disease or disorder mediated by CRTH2 and/or one or more other $PGD_2$ receptors, comprising administering to a subject having or being suspected to have such a condition or disease, a therapeutically effective amount of particulates of {4,6-bis(dimethylamino)-2-(4-(4-(trifluoromethyl)benzamido)-benzyl)pyrimidin-5-yl}acetic acid in an amorphous form, or crystalline Form I or II.

In yet another embodiment, provided is a method for treating, preventing, or ameliorating one or more symptoms of an eosinophil-related disease, comprising administering to a subject having or being suspected to have such a condition or disease, a therapeutically effective amount of particulates of {4,6-bis(dimethylamino)-2-(4-(4-(trifluoromethyl)benzamido)-benzyl)pyrimidin-5-yl}acetic acid in an amorphous form, or crystalline Form I or II.

In yet another embodiment, provided is a method for treating, preventing, or ameliorating one or more symptoms of a basophil-related disease, comprising administering to a subject having or being suspected to have such a condition or disease, a therapeutically effective amount of particulates of {4,6-bis(dimethylamino)-2-(4-(4-(trifluoromethyl)-benzamido)-benzyl)pyrimidin-5-yl}acetic acid in an amorphous form, or crystalline Form I or II.

In still another embodiment, provided is a method for treating, preventing, or ameliorating one or more symptoms of an inflammatory disease, comprising administering to a subject having or being suspected to have such a condition or disease, a therapeutically effective amount of particulates of {4,6-bis (dimethylamino)-2-(4-(4-(trifluoromethyl)-benzamido)-benzyl)pyrimidin-5-yl}acetic acid in an amorphous form, or crystalline Form I or II.

The disorders and diseases treatable with the particulates provided herein include, but are not limited to, (1) inflammatory or allergic diseases, including systemic anaphylaxis and hypersensitivity disorders, atopic dermatitis, urticaria, drug allergies, insect sting allergies, food allergies (including celiac disease and the like), and mastocytosis; (2) inflammatory bowel diseases, including Crohn's disease, ulcerative colitis, ileitis, and enteritis; (3) vasculitis, and Behcet's syndrome; (4) psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; (5) asthma and respiratory allergic diseases, including allergic asthma, exercise induced asthma, allergic rhinitis, otitis media, allergic conjunctivitis, hypersensitivity lung diseases, and chronic obstructive pulmonary disease; (6) autoimmune diseases, including arthritis (including rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma; and (20) infectious diseases, including HIV.

In certain embodiments, the disease is selected from the group consisting of asthma, allergic asthma, exercise induced asthma, allergic rhinitis, perennial allergic rhinitis, seasonal allergic rhinitis, atopic dermatitis, contact hypersensitivity, contact dermatitis, conjunctivitis, allergic conjunctivitis, eosinophilic bronchitis, food allergies, eosinophilic gastroenteritis, inflammatory bowel disease, ulcerative colitis, Crohn's disease, mastocytosis, hyper IgE syndrome, systemic lupus erythematous, psoriasis, acne, multiple sclerosis, allograft rejection, reperfusion injury, chronic obstructive pulmonary disease, Churg-Strauss syndrome, sinusitis, basophilic leukemia, chronic urticaria, basophilic leukocytosis, psoriasis, eczema, COPD (chronic obstructive pulmonary disorder), arthritis, rheumatoid arthritis, psoriatic arthritis, and osteoarthritis.

In certain embodiments, the disease is asthma, exercise induced asthma, allergic rhinitis, atopic dermatitis, chronic obstructive plumonary disease, or allergic conjunctivitis.

In certain embodiments, the disease is Churg-Strauss syndrome or sinusitis.

Depending on the disease to be treated and the subject's condition, the particulates or compositions provided herein may be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration and may be formulated, alone or together, in suitable dosage unit with pharmaceutically acceptable carriers, adjuvants and vehicles appropriate for each route of administration. Also provided is administration of the particulates provided herein in a depot formulation, in which the active ingredient is released over a pre-defined time period.

In the treatment, prevention, or amelioration of one or more symptoms of asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, or other conditions, disorders or diseases associated with CRTH2 and/or one or more other $PGD_2$ receptors, an appropriate dosage level generally is about 0.001 to 100 mg per kg patient body weight per day (mg/kg per day), about 0.01 to about 75 mg/kg per day, about 0.1 to about 50 mg/kg per day, about 0.5 to about 25 mg/kg per day, or about 1 to about 20 mg/kg per day, which may be administered in single or multiple doses. Within this range the dosage may be 0.005 to 0.05, 0.05 to 0.5, or 0.5 to 5.0, 1 to 15, 1 to 20, or 1 to 50 mg/kg per day. In certain embodiments, the dosage level is about 0.001 to 100 mg/kg per day. In certain embodiments, the dosage level is about 0.01 to about 75 mg/kg per day. In certain embodiments, the dosage level is about 0.1 to about 50 mg/kg per day. In certain embodiments, the dosage level is about 0.5 to about 25 mg/kg per day. In certain embodiments, the dosage level is about 1 to about 20 mg/kg per day.

For oral administration, the pharmaceutical compositions can be provided in the form of tablets containing 1.0 to 1,000 mg of the active ingredient, particularly about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The compositions may be administered on a regimen of 1 to 4 times per day, including once, twice, three times, and four times per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also provided herein are methods of modulating CRTH2 and/or one or more other $PGD_2$ receptors, comprising contacting the receptor(s) with the particulates in one or more solid forms as provided herein. In one embodiment, the receptor(s) are expressed by a cell.

The particulates provided herein may also be combined or used in combination with other agents useful in the treatment, prevention, or amelioration of one or more symptoms of the diseases or conditions for which the particulates provided herein are useful, including asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, and those pathologies noted above.

Such other agents, or drugs, may be administered, by a route and in an amount commonly used therefor, simultaneously or sequentially with the particulates provided herein. When an the particulates provided herein are used contemporaneously with one or more other drugs, a pharmaceutical composition containing such other drugs in addition to the particulates provided herein may be utilized, but is not required. Accordingly, the pharmaceutical compositions provided herein include those that also contain one or more other active ingredients or therapeutic agents, in addition to particulates provided herein.

The weight ratio of the particulates provided herein to the second active ingredient may be varied, and will depend upon the effective dose of each ingredient. Generally, an effective dose of each will be used. Thus, for example, when the particulates provided herein are combined with a NSAID, the weight ratio of the particulates to the NSAID may range from about 1,000:1 to about 1:1,000, or about 200:1 to about 1:200. Combinations of the particulates provided herein and other active ingredients will generally also be within the aforementioned range, but in each case, an effective dose of each active ingredient should be used.

EXAMPLES

The particulates of the acid of Formula I in the following examples were characterized with X-ray powder diffractometry (XRPD), differential scanning calorimetry (DSC), thermogravimetry (TGA), and scanning electron microscopy (SEM).

X-ray powder diffraction data was recorded with a Rigaku MiniFlex X-ray powder diffractometer (Rigaku Americas, The Woodlands, Tex.). The radiation was CuKa (40 kV, 40 mA). Data were collected at room temperature from 3 to 45 degrees two-theta at 0.02 degrees per step and 0.6 sec per step. Samples were prepared on glass specimen holders as a thin layer of powdered material without solvent.

Differential scanning calorimetry was carried out using a Mettler 850, TA 2920. Samples were place in sealed aluminum pans for analysis with an empty aluminum pan as the reference. A heating rate of 10° C./min was employed over a temperature range from 30° C. to 280° C.

The thermogravimetric analysis was also conducted on a Mettler 850, TA 2920. Samples were placed into a ceramic or aluminum sample pan. A heating rate of 20° C./min was employed over a temperature range from 20° C. to 600° C.

Example 1

Determination of Solubilities of {4,6-Bis(dimethylamino)-2-(4-(4-(trifluoromethyl)benzamido)benzyl)pyrimidin-5-yl}Acetic Acid Saturated solutions of {4,6-bis(dimethylamino)-2-(4-(4-(trifluoromethyl)-benzamido)benzyl)pyrimidin-5-yl}acetic acid of Formula I in the solvents listed in Table 1 were prepared from the acid predominantly in Form I, at both 25 and 50° C. The concentration of each saturated solution was determined using HPLC and the results are summarized in Table 1.

Example 2

Preparation of {4,6-Bis(dimethylamino)-2-(4-(4-(trifluoromethyl)benzamido)benzyl)pyrimidin-5-yl}Acetic Acid of Form I A slurry of {4,6-bis(dimethylamino)-2-(4-(4-(trifluoromethyl)benzamido)-benzyl)pyrimidin-5-yl}acetic acid in methanol was stirred overnight at room temperature. The particulates were then filtered, washed with hexane, and dried.

The X-ray powder diffraction pattern of the particulates is illustrated in FIG. 1. The particulates have characteristic XRP diffraction peaks expressed in two-theta at approximately 9.8, 13.1, 22.0, and 26.4°, suggesting that the particulates are crystalline. As shown in FIG. 4, the particulates are long acicular crystals with a size of about 1 to about 5 μm.

The differential scanning calorimetric thermogram of the particulates is illustrated in FIG. 2. The particulates exhibit an endotherm with a peak temperature of 223.8° C. and an onset temperature of 220.2° C.

Figure 3:
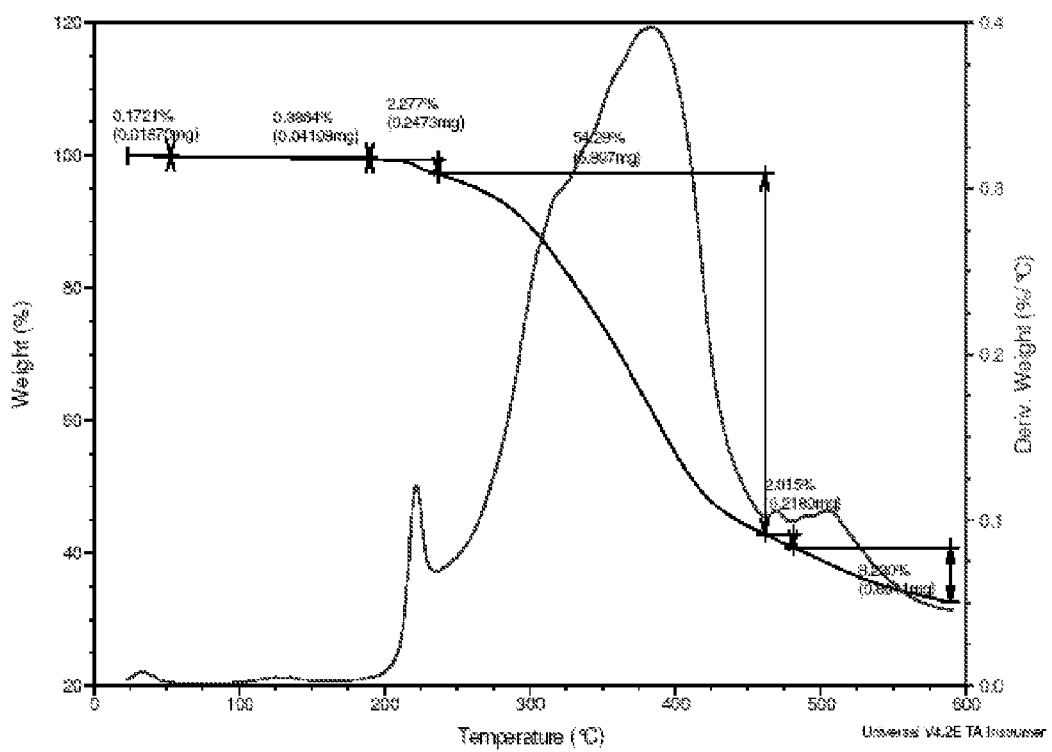
FIG. 3 depicts a thermogravimetric (TG) thermogram of the particulates of the acid of Formula I in Form I.

The thermogravimetric analysis thermogram of the particulates in Form I is shown in FIG. 3. The particulate is very stable and shows no significant weight loss until decomposition around 200° C.

Figure 5:
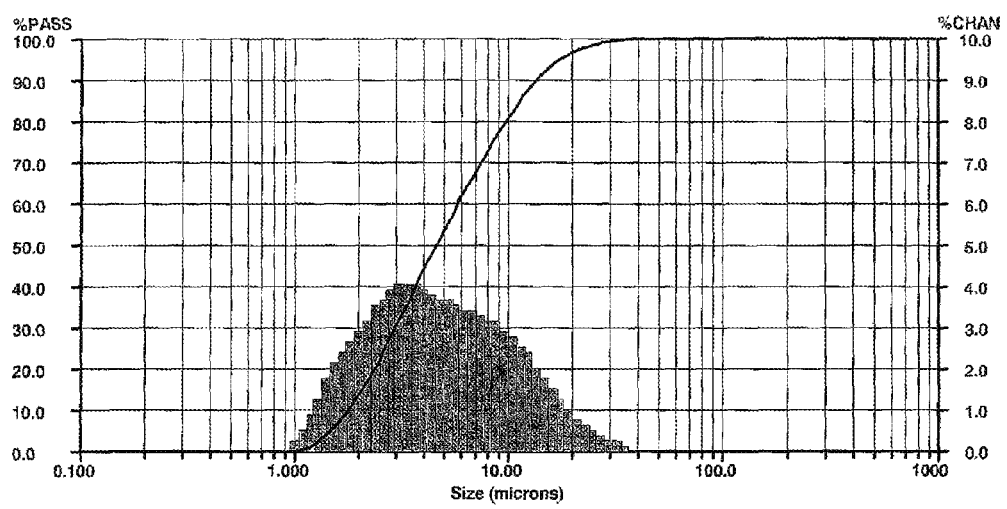
FIG. 5 depicts a particle size distribution graph of the particulates of the acid of Formula I in Form I.

The average particle size and particle size distribution of the particulates in Form I were measured using a Microtrac S3000 (Microtrac Inc., Montgomeryville, Pa.). The results are shown in FIG. 5 and summarized in Table 2. The particulates in Form I have an average particle size (MV) of 6.495 μm and a uniformity coefficient of 3.24.

TABLE 1

SOLUBILITY

| Solvent | Solubility (mg/mL) | |
|---|---|---|
| | 25° C. | 50° C. |
| Acetonitrile | 0.24 | 0.94 |
| Chloroform | 0.17 | 0.35 |
| Dichloromethane | 0.07 | |
| DMF | >50 | >50 |
| 1,4-Dioxane | 3.37 | 9.83 |
| Methanol | 2.23 | 3.04 |
| 2-Methoxyethanol | 5.35 | 8.55 |
| MIBK | 0.54 | 1.80 |
| Toluene | 0.00 | 0.03 |
| Hexane | 0.00 | 0.00 |
| Acetone | 2.62 | 3.34 |
| n-Butanol | 0.79 | 2.11 |
| MTBE | 0.09 | 0.41 |
| DMSO | >50 | >50 |
| Ethanol | 1.09 | 2.25 |
| Ethyl acetate | 0.53 | 1.27 |
| Ethyl formate | 0.39 | 1.51 |
| Heptane | 0.00 | 0.00 |
| Isobutyl acetate | 0.20 | 0.83 |
| Isopropyl acetate | 0.27 | 0.78 |
| 1-Propanol | 0.79 | 2.41 |
| Isopropanol | 0.77 | 1.96 |
| Water | 0.00 | 0.02 |
| MEK | 1.98 | 4.26 |
| THF | 11.32 | 32.72 |

TABLE 2

PARTICLE SIZE DISTRIBUTION

| Percentiles | Particle size (μm) |
|---|---|
| 10 | 1.807 |
| 20 | 2.393 |
| 30 | 3.004 |
| 40 | 3.713 |
| 50 | 4.627 |
| 60 | 5.852 |
| 70 | 7.498 |
| 80 | 9.825 |

TABLE 2-continued

PARTICLE SIZE DISTRIBUTION

| Percentiles | Particle size (μm) |
|---|---|
| 90 | 13.70 |
| 95 | 17.57 |

Example 3

Preparation of {4,6-Bis(dimethylamino)-2-(4-(4-(trifluoromethyl)benzamido)benzyl)pyrimidin-5-yl}Acetic Acid in Form II A solution of {4,6-bis(dimethylamino)-2-(4-(4-(trifluoromethyl)benzamido)-benzyl)pyrimidin-5-yl}acetic acid (50 mg) in DMF (0.5 mL) was prepared from the acid predominantly in Form I. The solution was then added to 8 mL of MTBE at room temperature. After stirred at room temperature for additional 15 min, the mixture became slurry. The particulates were then filtered, washed with hexane, and dried.

The X-ray powder diffraction pattern of the particulates is illustrated in FIG. 6. The particulates have a characteristic XRP diffraction peak expressed in two-theta at approximately 31.7°, suggesting that the particulates are in a crystalline form (Form II) that is different from Form I. The crystalline habits of the particulates of Form II are shown in FIG. 7.

Example 4

Phase Equilibration

Based on the solubilities of {4,6-bis(dimethylamino)-2-(4-(4-(trifluoromethyl)benzamido)-benzyl)pyrimidin-5-yl}acetic acid in various solvents as determined in Example 1, particulates of the acid predominately in Form I was exposed to a solvent listed in Table 3 at either 25 or 50° C. for a sufficient period of time. The particulates were filtrated and dried, and then analyzed using XRPD. The results are summarized in Table 3.

Example 5

Phase Equilibration Between Form I and Form II

Figure 8:
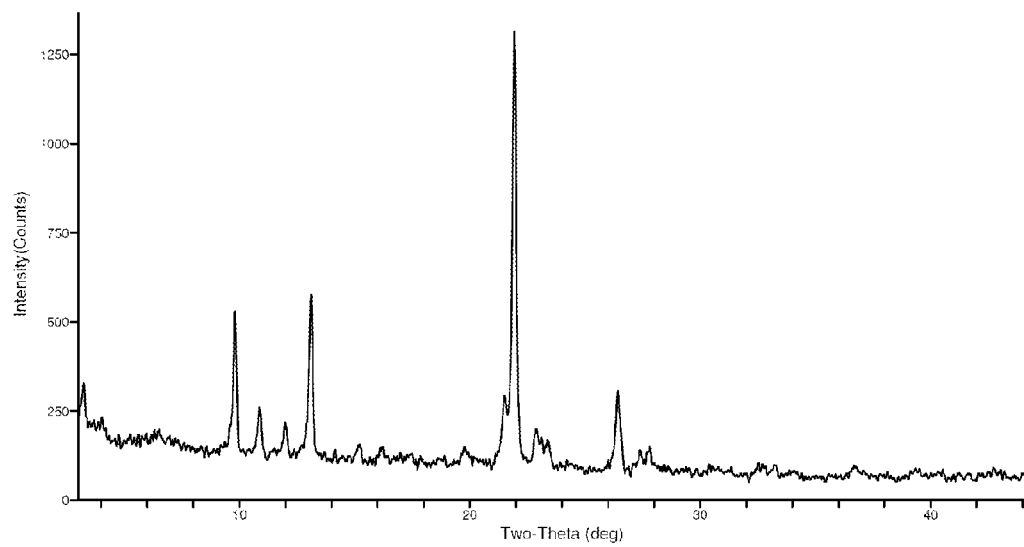
FIG. 8 depicts an XRP diffractogram of the particulates of the acid of Formula I obtained through phase equilibration between particulates of Form I and Form II.

Particulates of Form II were prepared as slurry, as described in Example 2. Briefly, a solution of {4,6-bis(dimethylamino)-2-(4-(4-(trifluoromethyl)benzamido)benzyl)-pyrimidin-5-yl}acetic acid (50 mg) in DMF (0.5 mL) was added to 8 mL of MTBE to generate a slurry of particulates of Form II. Particulates of Form I (20 mg) was then added to the slurry and the resulting slurry was stirred overnight at room temperature. The particulates were then filtered, washed with hexane, and dried. The particulates were analyzed using XRPD. The XRP diffractogram is shown in FIG. 8, indicating that the particulates after phase equilibration were Form I.

Example 6

Particulate Formation Via Solvent Evaporation

Based on the solubility of {4,6-bis(dimethylamino)-2-(4-(4-(trifluoromethyl)-benzamido)benzyl)pyrimidin-5-yl}acetic acid in various solvents as determined in Example 1, the acid predominately in Form I were dissolved in a solvent system listed in Table 4. The solvent was allowed to evaporate from the solution at 25 or 50° C. The resulting particulates were collected by filtration and analyzed using XRPD. The results are summarized in Table 4.

TABLE 3

CRYSTALLINE FORM AFTER PHASE EQUILIBRATION

| | Polymorph | |
|---|---|---|
| Solvent | 25° C. | 50° C. |
| Acetonitrile | Form I | Form I |
| Chloroform | Form I | Form I |
| Dichloromethane | Form I | |
| DMF | NA[a] | |
| 1,4-Dioxane | Form I | Form I |
| Methanol | Form I | Form I |
| 2-Methoxyethanol | Form I | Form I |
| MIBK | Form I | Form I |
| Toluene | Form I | Form I |
| Hexane | Form I | Form I |
| Acetone | Form I | Form I |
| n-Butanol | Form I | Form I |
| MTBE | Form I | Form I |
| DMSO | NA | |
| Ethanol | Form I | Form I |
| Ethyl acetate | Form I | Form I |
| Ethyl formate | Form I | Form I |
| Heptane | Form I | Form I |
| Isobutyl acetate | Form I | Form I |
| Isopropyl acetate | Form I | Form I |
| 1-Propanol | Form I | Form I |
| Isopropanol | Form I | Form I |
| Water | Form I | Form I |
| MEK | Form I | Form I |
| THF | Form I | Form I |

[a]NA: not available. The sample did not produce any or enough solids

Example 7

Particulate Formation Via Anti-Solvent Addition

Saturated solutions of the acid of Formula I in the solvents listed in Table 5 were prepared from the acid predominately in Form I. An anti-solvent was then added to the saturated solutions to induce precipitation. THF, 2-methoxyethanol, DMSO, and DMF were used as solvents to dissolve the particulates of Form I, whereas hexane, MTBE, toluene, and water were used as anti-solvents. The resulting particulates were collected by filtration and analyzed using XRPD. The results are summarized in Table 5.

Example 8

Particulate Formation Via Reverse Anti-Solvent Addition

Saturated or near saturated solutions of the acid of Formula I in the solvents listed in Table 6 were prepared from the acid predominately in Form I. The solutions were then each added to a larger volume of a miscible anti-solvent. THF, 2-methoxyethanol, DMSO, and DMF were used as solvents to dissolve the particulates, whereas hexane, MTBE, toluene, and water were used as anti-solvents. The resulting particulates were collected by filtration and analyzed using XRPD. The results are summarized in Table 6.

Example 9

Particulate Formation Via Quench Cool

Saturated solutions of the acid of Formula I in the solvents listed in Table 7 were prepared from the acid predominately in Form I, at about 30 to 50° C. The solutions were quench cooled in an acetone/ice bath. The resulting particulates were collected by filtration and analyzed using XRPD. The results are summarized in Table 7.

TABLE 4

CRYSTALLINE FORM FROM SOLVENT EVAPORATION

| Solvent | Polymorph 25° C. | Polymorph 50° C. |
|---|---|---|
| Acetonitrile | Form I | Form I |
| Chloroform | NA[a] | NA |
| Dichloromethane | NA | |
| DMF | Form I | Form I |
| 1,4-Dioxane | Form I | Form I |
| Methanol | Form I | Form I |
| 2-Methoxyethanol | Form I | Form I |
| MIBK | Form I | Form I |
| Toluene | NA | NA |
| Hexane | NA | NA |
| Acetone | Form I | Form I |
| n-Butanol | NA | Form I |
| MTBE | NA | Form I |
| DMSO | Form I | Form I |
| Ethanol | Form I | Form I |
| Ethyl acetate | Form I | Form I |
| Ethyl formate | Amorphous | NA |
| Heptane | NA | NA |
| Isobutyl acetate | Form I | Form I |
| Isopropyl acetate | Form I | Form I |
| 1-Propanol | Form I | Form I |
| Isopropanol | Form I | Form I |
| Water | NA | NA |
| MEK | Form I | Form I |
| THF | Form I | Form I |

[a]NA: not available. The sample did not produce any or enough solids

TABLE 5

CRYSTALLINE FORM FROM ANTI-SOLVENT ADDITION

| Solvent | Anti-solvent | Polymorph |
|---|---|---|
| THF | Hexane | Form I |
| THF | MTBE | NA[a] |
| THF | Toluene | NA |
| THF | Water | Form I |
| 2-Methoxyethanol | Hexane | NA |
| 2-Methoxyethanol | MTBE | NA |
| 2-Methoxyethanol | Toluene | NA |
| 2-Methoxyethanol | Water | NA |
| DMSO | Hexane | NA |
| DMSO | MTBE | NA |
| DMSO | Toluene | NA |
| DMSO | Water | Mostly amorphous |
| DMF | Hexane | NA |
| DMF | MTBE | Small amount (?) |
| DMF | Toluene | NA |
| DMF | Water | Form I |

[a]NA: not available. The sample did not produce any or enough solids

Example 10

Particulates Via Crystallization with Heating and Cooling Cycles

Saturated solutions of the acid of Formula I in the solvents listed in Table 8 were prepared from the acid predominantly in Form I, at about 30 to 50° C. The solutions were cooled slowly using a programmable circulating bath to form slurry. Then, the resulting slurry was first heated to 50° C. over 2 hr, followed by cooling down to 25° C. for 2 hr. This heating and cooling process was repeated overnight. The resulting particulates were then collected by filtration and analyzed using XRPD. The results are summarized in Table 8.

TABLE 6

CRYSTALLINE FORM FROM REVERSE ANTI-SOLVENT ADDITION

| Solvent | Anti-solvent | Polymorph |
|---|---|---|
| THF (1 mL) | Hexane (4 mL) | Form I |
| THF (0.5 mL) | MTBE (8 mL) | NA[a] |
| THF (0.5 mL) | Toluene (8 mL) | NA |
| THF (0.5 mL) | Water (4 mL) | Form I |
| 2-Methoxyethanol (0.5 mL) | Hexane (8 mL) | Form I |
| 2-Methoxyethanol (0.5 mL) | MTBE (8 mL) | NA |
| 2-Methoxyethanol (0.5 mL) | Toluene (8 mL) | NA |
| 2-Methoxyethanol (0.5 mL) | Water (8 mL) | NA |
| DMSO (0.5 mL) | Hexane (8 mL) | NA |
| DMSO (0.5 mL) | MTBE (8 mL) | Small amount (?) |
| DMSO (0.5 mL) | Toluene (8 mL) | NA |
| DMSO (1 mL) | Water (4 mL) | Form I |
| DMF (0.5 mL) | Hexane (8 mL) | NA |
| DMF (0.5 mL) | MTBE (8 mL) | Form II |
| DMF (0.5 mL) | Toluene (8 mL) | NA |
| DMF (1 mL) | Water (4 mL) | Form I |

[a]NA: not available. The sample did not produce any or enough solids

TABLE 7

CRYSTALLINE FORM QUICK COOL

| Solvent | Polymorph |
|---|---|
| DMF | NA[a] |
| 1,4-Dioxane | NA |
| 2-Methoxyethanol | NA |
| Acetonitrile | Form I |
| Methanol | Form I |
| n-Butanol | NA |
| 1-Propanol | Form I |
| Isopropanol | NA |
| MEK | Form I |
| THF | NA |

[a]NA: not available. The sample did not produce any or enough solids

TABLE 8

CRYSTALLINE FORM FOR EVAPORATION

| Solvent | Polymorph |
|---|---|
| Acetonitrile | Form I |
| 1,4-Dioxane | Form I |
| 2-Methoxyethanol | Form I |
| MIBK | Form I |
| Acetone | Form I |
| n-Butanol | Form I |
| Ethanol | Form I |
| 1-Propanol | Form I |
| Isopropanol | Form I |
| Water/THF (3:7, v/v) | Form I |

TABLE 8-continued

CRYSTALLINE FORM FOR EVAPORATION

| Solvent | Polymorph |
|---|---|
| MEK | Form I |
| THF | Form I |

Example 11

Competitive Radioligand Binding Assay

The binding affinity and selectivity of the amine salts of 4,6-bis(dimethylamino)-2-(4-(4-(trifluoromethyl)benzamido)benzyl)pyrimidin-5-yl}acetic acid provided herein were evaluated using a competitive radioligand binding assay with stably-transfected cell lines expressing CRTH2 or DP1.

Prostaglandin $D_2$ and 13,14-dihydro-15-keto $PGD_2$ were obtained from Cayman Chemical (Ann Arbor, Mich.). Radiolabelled $PGD_2$ (5,6,8,9,12,14,15-$^3$H(N)) with a specific activity of 160 Ci/mmol was obtained from PerkinElmer (Boston, Mass.). Cell culture medium RPMI 1640, HEPES buffer, phosphate buffered saline (PBS), L-glutamine, and penicillin-streptomycin solution were obtained from Mediatech Inc. (Herndon, Va.). Fetal calf serum (FCS) was obtained from Cambrex (Walkersville, Md.). Puromycin was obtained from Invitrogen (San Diego, Calif.). Poly(ethyleneimine) (PEI) was obtained from Acros Organics (Morris Plains, N.J.). Purified monoclonal rat anti-human CRTH2 antibody (BM16), Rat IgG2a, κ, (clone R35-95), and goat anti-rat Ig-FITC were obtained from Becton Dickinson Biosciences (San Diego, Calif.). BSA (Fraction V) and sodium azide were obtained from Sigma Chemical Company (St. Louis).

The CRTH2 and DP1 stable cell lines were generated according to the procedure described by Sugimoto et al. (J. Pharm. Exp. Therap. 2003, 305, 347-352). These cell lines were maintained in RPMI 1640 culture medium containing HEPES buffer (25 mM), FCS (10%), L-glutamine (2 mM), penicillin (10 IU/mL), streptomycin (100 μg/mL), and puromycin (1 μg/mL).

The surface expression of CRTH2 on the transfected cell lines was monitored periodically during culture and prior to each competitive radioligand binding assay. The CRTH2 expressing cells and untransfected cells were incubated on ice with either purified anti-CRTH2 antibody (clone BM16) or an isotype control antibody (Rat IgG2a, κ) for 15 min. The cells were then washed in 2 mL of FACS buffer (PBS containing 1% BSA (Fraction V) and 0.1% sodium azide. The cells were subsequently incubated on ice with a FITC-conjugated anti-rat antibody (goat anti-rat Ig-FITC). After washed with cold FACS buffer, the cells were analyzed using a FACScan II analyzer and CellQuest software, both from Becton Dickinson (Mountain View, Calif.).

The functionality of the receptor transfectants were also assessed by direct measure of calcium mobilization in response to $PGD_2$ as described (Sugimoto et al., J. Pharm. Exp. Therap. 2003, 305, 347-352; Sugimoto et al., Eur. J. Pharmacol. 2005, 524, 30-37).

Radioligand binding analyses were performed according to the methods of Sugimoto et al. (J. Pharm. Exp. Therap. 2003, 305, 347-352; Eur. J. Pharmacol. 2005, 524, 30-37). The test compounds were dissolved in DMSO at a concentration of 100 mM as stock solutions. Serial dilutions from 10 μM were made in binding buffer prior to assay. Transfected cells were resuspended in binding buffer (50 mM Tris-HCl, 40 mM MgCl$_2$, and 0.1% bovine serum albumin, at pH 7.4) at a concentration of 4×10$^6$/mL at room temperature. Transfected cells were then seeded in U-bottom polypropylene 96-well plates (Fisher) by adding 50 μL of the cell suspension, followed by addition of 10 μL of $^3$H-PGD$_2$, 10 μL of the test compound solutions at a series of concentrations or controls, 30 μL of the binding buffer to bring the final volume to 100 μL. The final concentration of $^3$H-PGD$_2$ in each well was 1 nM. After incubated for 1 hr at room temperature with gentle shaking, the cell suspension was transferred to filtration plates (Millipore, Mass.), which were pre-wetted with 0.5% PEI buffer. The cell pellets were washed three times with the binding buffer and the plates were allowed to air dry. Scintillant (50 μL; Microscint™ 20, Perkin Elmer, Boston, Mass.) was added to each well and the radioactivity was counted on a TopCount (Packard Bioscience, Meriden, Conn.). Data analyses were performed using the Prizm™ graphics program (GraphPad Software Inc., San Diego, Calif.). As shown in FIGS. 10 and 11, 4,6-bis(dimethylamino)-2-(4-(4-(trifluoromethyl)benzamido)benzyl)pyrimidin-5-yl}acetic acid of Formula I has a high affinity for and binds selectively to CRTH2.

The examples set forth above are provided to give those of ordinary skill in the art with a complete disclosure and description of how to make and use the embodiments, and are not intended to limit the scope of the disclosure. Modifications of the above-described modes for carrying out the disclosure that are obvious to persons of skill in the art are intended to be within the scope of the following claims. All publications, patents, and patent applications cited in this specification are incorporated herein by reference as if each such publication, patent, or patent application were specifically and individually indicated to be incorporated herein by reference.

What is claimed is:

1. Particulates of {4,6-bis(dimethylamino)-2-(4-(4-(trifluoromethyl)benzamido)-benzyl)pyrimidin-5-yl}acetic acid of Formula I:

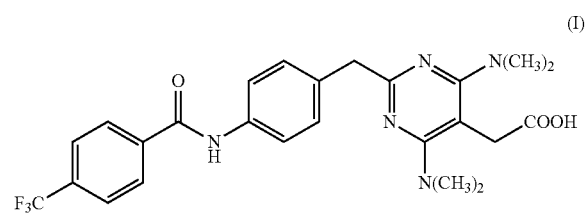 [SMILES: CN(C)c1nc(Cc2ccc(NC(=O)c3ccc(C(F)(F)F)cc3)cc2)nc(N(C)C)c1CC(=O)O]

(I)

in crystalline Form I; wherein the particulates have one or more characteristics, selected from the group consisting of:
(i) having an average particle size ranging from about 0.1 to about 150 μm;
(ii) having a uniformity coefficient ranging from about 1 to about 20;
(iii) having a tapped bulk density ranging from about 0.1 to about 1.0 g/mL;
(iv) containing no less than about 95% by weight of the acid of Formula I;
(v) having a residual organic solvent content of no greater than about 5% by weight;
(vi) having a residual methanol content of no greater than about 100,000 ppm;
(vii) containing no less than about 90% by weight of the particulates in Form I; and wherein the particulates have a differential scanning calorimetric thermogram with an endotherm at a peak temperature of about 224° C. and an onset temperature of about 220° C.

2. The particulates of claim 1, wherein the particulates have an X-ray powder diffraction pattern with one or more peaks expressed in two-theta at approximately 9.8, 13.1, 22.0, and 26.4°.

3. The particulates of claim 1, wherein the particulates have an X-ray powder diffraction pattern with a peak expressed in two-theta at approximately 22.0±0.1°.

4. The particulates of claim 1, wherein the crystal habit of the particulates is acicular.

5. The particulates of claim 1, having an aqueous solubility of about 3 μg/mL at room temperature.

6. The particulates of claim 1, wherein the particulates have a uniformity coefficient ranging from about 1 to about 20.

7. The particulates of claim 1, wherein the particulates have a residual organic solvent content of no greater than about 5% by weight.

8. A pharmaceutical composition comprising the particulates of claim 1, and a pharmaceutically acceptable carrier.

9. The pharmaceutical composition of claim 8, wherein the composition is formulated for oral, nasal, bronchial, or topical administration.

10. The pharmaceutical composition of claim 8, wherein the composition is formulated as a single dosage form.

11. 4,6-Bis(dimethylamino)-2-(4-(4-(trifluoromethyl)benzamido)-benzyl)pyrimidin-5-yl}acetic acid in crystalline Form I; wherein the crystalline form has an X-ray powder diffraction pattern with one or more peaks expressed in two-theta at approximately 9.8, 13.1, 22.0, and 26.4°; and wherein the particulates have a differential scanning calorimetric thermogram with an endotherm at a peak temperature of about 224° C. and an onset temperature of about 220° C.

* * * * *